US005843888A

United States Patent [19]
Ho et al.

[11] Patent Number: 5,843,888
[45] Date of Patent: Dec. 1, 1998

[54] LOW OXYGEN AFFINITY MUTANT HEMOGLOBIN

[75] Inventors: Chien Ho; Hyun-Won Kim; Tong-Jian Shen, all of Pittsburgh, Pa.

[73] Assignee: Carnegie Mellon University, Pittsburgh, Pa.

[21] Appl. No.: 432,071

[22] Filed: May 1, 1995

[51] Int. Cl.$^6$ .......................... C07K 14/805; C07H 21/06
[52] U.S. Cl. ................. 514/6; 530/385; 435/69.1
[58] Field of Search ................... 530/385; 435/69.1, 435/243, 325, 320.1; 514/12, 6

[56] References Cited

U.S. PATENT DOCUMENTS

| | | |
|---|---|---|
| 4,865,974 | 9/1989 | Ben-Bassat et al. . |
| 4,870,017 | 9/1989 | Ben-Bassat et al. . |
| 5,013,662 | 5/1991 | Ben-Bassat et al. . |
| 5,028,588 | 7/1991 | Hoffman et al. ............................ 514/6 |

OTHER PUBLICATIONS

Ho et al. 1994 Biophys. T. 66 (2pt2): A269.
Tame et al 1991 J Mol. Biol 218: 761–767.
Kim et al 1995 J. Mol. Biol 248(1): 867–882.
Mulder, A.G., et al., *J. Cell. Comp. Physiol.* 5:383 (1934).
Bunn, H.F., et al., *J. Exp. Med.* 129:909 (1969).
Chada, K., et al., *Nature (London)* 314:377 (1985).
Townes, T.M., et al., *EMBO J.* 4:1715 (1985).
Swanson, M.E., et al., *Bio/Technology* 10:557 (1992).
Groebe, D.R., et al., *Protein Expression and Purification* 3:134 (1992).
Wagenbach, M., et al., *Bio/Technology* 9:57 (1991).
DeLlano, J.J., et al., *Proc. Natl. Acad. Sci. USA* 90:918 (1993).
Hoffman, S.J., et al., *Proc. Natl. Acad. Sci. USA* 87:8521 (1990).
Hernan, R.A., et al., *Biochemistry* 31:8619 (1992).
Shen, T.–J., et al., *Proc. Natl. Acad. Sci. USA* 90:8108 (1993).
Nagai, K., et al., *Nature (London)* 309:810 (1984).
Nagai, K., et al, *Methods Enzymol.* 153:461 (1987).
Bunn, H.F., et al., *Hemoglobin: Molecular, Genetic and Clinical Aspects* (Saunders, Philadelphia) pp. 37–60 (1986).
Kavanaugh, J.S., et al., *Biochemistry* 31:8640 (1992).
Ben–Bassat, A., et al., *J. Bacteriol.* 169:751 (1987).
Dickerson, R.E., et al., *Hemoglobin: Structure, Function, Evolutiion, and Pathology,* (The Benjamin Cummings Publishing Co., Menlo Park, CA) (1983).
Bunn, H.F., et al., *J. Biol. Chem.* 249:7402 (1974).
Perutz, M.F., et al., *Mechanisms of Cooperativity and Allosteric Regulation in Proteins,* Cambridge University Press (1990).
Reed, C.S., et al. *Blood* 31:623 (1968).
Jones, R.T., et al., *J. Clin. Invest.* 46:1840 (1967).
Weatherall, D.J., et al., *British J. Haematol.* 35:177 (1977).
Fermi, G., et al., *J. Mol. Biol.* 175:159 (1984).
Ishimori, K., et al., *J. Biol. Chem.* 264:14624 (1989).
Imai, K., et al., *J. Mol. Biol.* 218:769 (1991).
Shaanan, B., et al., *J. Mol. Biol.* 171:31 (1983).
Schneider, R.G., et al., *Biochim. Biophys. Acta.* 400:365 (1975).

Bonaventura, J., et al., *J. Biol. Chem.* 243:980 (1968).
Moo–Penn, W.F., et al., *FEBS Lett.* 92:53 (1978).
O'Donnell, J.K., et al., *J. Biol. Chem.* 269:27692 (1994).
Baudin, V., et al., *Biochim. Biophys. Acta.* 1159:223 (1992).
Dang, L.X., et al., *J. Am. Chem. Soc.* 111:8505 (1989).
Gao, J., et al., *Science* 244:1069 (1989).
Kim, H.–W., et al., *Proc. Natl. Acad. Sci. USA* 91:11547 (1994).
Kunkel, T.M., et al., *Proc. Natl. Acad. Sci. USA* 82:488 (1985).
Antonini, E., et al., *Hemoglobin and Myoglobin in Their Reactions with Ligands* (North Holland, Amsterdam) p. 19 (1971).
Lindstrom, T.R., et al., *Proc. Natl. Acad. Sci. USA* 69:1707 (1972).
Hewick, R.M., et al., *J. Biol. Chem.* 256:7990 (1981).
*Pure Appl. Chem.* 63:975 (1991).
Bunn, H.F., et al., *Hemoglobin: Molecular, Genetic and Clinical Aspects* (W.P. Saunders, Inc., Philadelphia, PA) pp. 634–662 (1986).
Ho, C., *Adv. Protein Chem.* 43:153 (1992).
Plateau, P., et al., *J. Am. Chem. Soc.* 104:7310 (1982).
Hayashi, A., et al., *Biochim. Biophys. Acta* 310:309 (1973).
Brooks, C.L., et al., *J. Mol. Biol.* 208:159 (1989).
Jorgensen, W.L., et al., *J. Chem. Phys.* 79:926 (1983).
Ponder, J.W., et al., *J. Mol. Biol.* 193:775 (1987).
Tidor, B., et al., *Biochemistry* 30:3217.
Ryckaert, J.–P., et al., *J. Comput. Phys.* 23:327 (1977).
Kirkwood, J.G., *J. Chem. Phys.* 3:300 (1935).
Brooks, C.L., et al., *J. Phys. Chem.* 90:6680 (1986).
Lindstrom, T.R., et al., *Biochemistry* 11:1677 (1972).
Dalvit, C., et al., *Biochemistry* 24:3398 (1985).
Takashashi, S., et al., *Biochemistry* 19:5196 (1980).
La Mar, G.N., et al., *Biochem. Biophys. Res. Commun.* 96:1172 (1980).
Fung, L.W.–M., et al., *Biochemistry* 14:2526 (1975).
Jesson, J.P., *J. Chem. Phys.* 47:579 (1967).
Kurland, R.J., et al., *J. Magn. Reson.* 2:286 (1970).
Johnson, M.E., et al., *J. Am. Chem. Soc.* 99:1245 (1977).
Turner, G.J., et al., *Proteins* 14:133 (1992).
Winslow, R.M., et al., eds. *Blood Substitutes Physiological Basis of Efficacy* (Birkauser, Boston, MA) pp. 82–84 (1995).
Manning, L.R., et al., *Biochemistry* 27:6640 (1988).
Benesch, R.E., et al., *Biochem. Biophys. Res. Comm.* 156:9 (1988).
Bucci, E., et al., *J. Biol. Chem.* 264:6191 (1989).
Chang, T.M.S., et al., eds. Proceeding of II International Symposium on Blood Substitutes, *Biomater. Artif. Cells Artif. Organs* (1988).
Kluger, R., et al., *Biochemistry* 31:7551 (1992).
DeVenuto, F., et al., *Surg. Gynecol. Obstet.* 155:342 (1982).

*Primary Examiner*—Karen Cochrane Carlson
*Attorney, Agent, or Firm*—Reed Smith Shaw & McClay LLP

[57] ABSTRACT

A non-naturally occurring mutant hemoglobin ($\alpha$96Val→Trp) is provided that has a lower oxygen affinity than that of native hemoglobin, but high cooperativity in oxygen binding. The mutant hemoglobin is preferably obtained by recombinant DNA techniques. Such a mutant hemoglobin may be used as a component of a blood substitute.

15 Claims, 11 Drawing Sheets

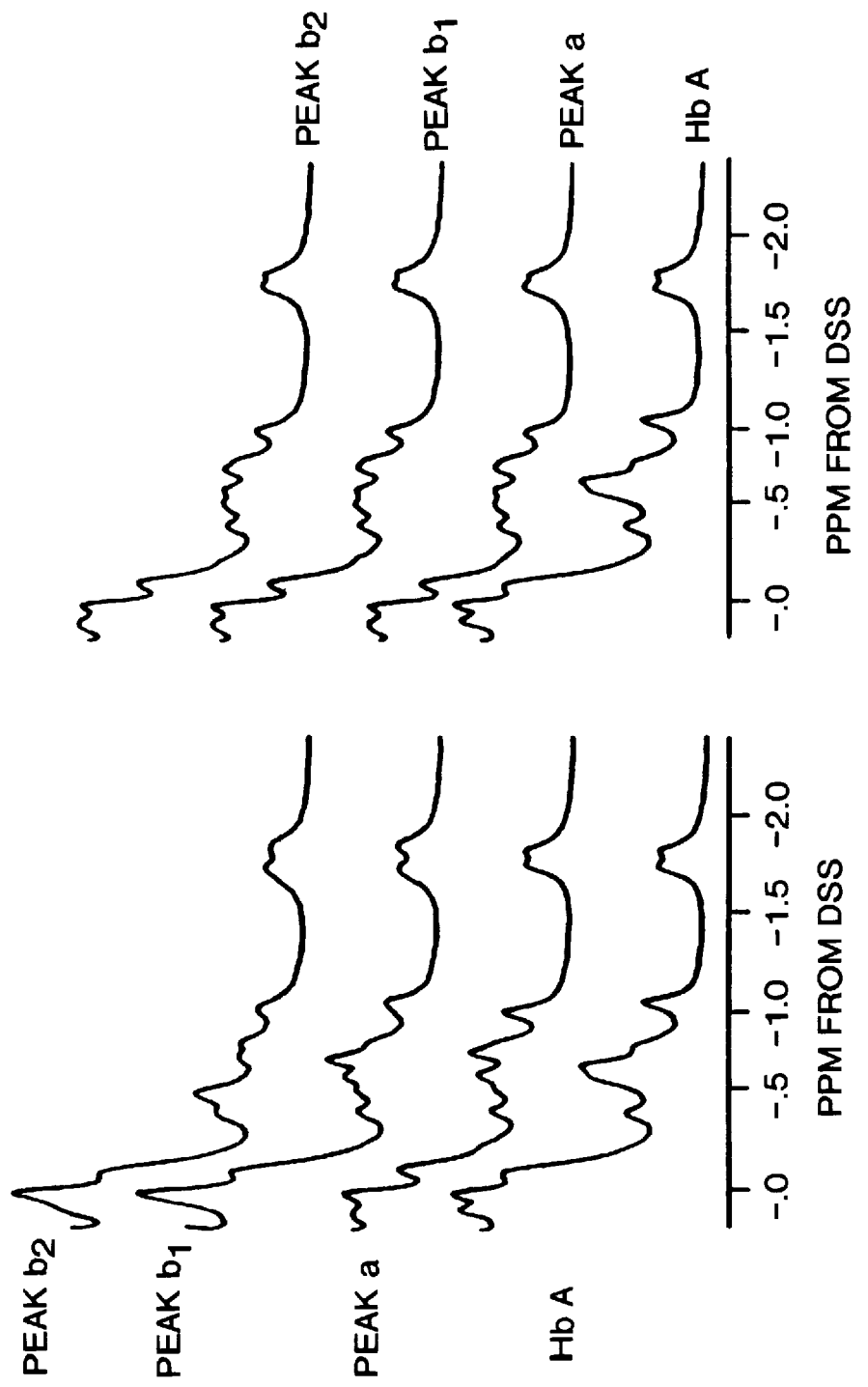

FIG. 11A

EXCHANGEABLE PROTON RESONANCES r Hb (α96 Val→Trp) pHE 702 DERIVED FROM (PEAK 2)

r Hb (α96 Val→Trp) pHE 202 DERIVED FROM (PEAK b$_2$)

Hb A

PPM FROM DSS

FIG. 11B

RING-CURRENT SHIFTED PROTON RESONANCES r Hb (α96 Val→Trp) pHE 702 DERIVED FROM (PEAK 2)

r Hb (α96 Val→Trp) pHE 202 DERIVED FROM (PEAK b$_2$)

Hb A

PPM FROM DSS

LOW OXYGEN AFFINITY MUTANT HEMOGLOBIN

ACKNOWLEDGMENT

The present invention was developed in part with government support under grant number HL-24525. The government has certain rights in this invention.

FIELD OF THE INVENTION

This invention relates generally to a novel mutant hemoglobin and more particularly relates to a recombinant mutant hemoglobin "r Hb (α96Val→Trp)" that shows a low oxygen affinity, but high cooperativity in oxygen binding. This invention further relates to the preparation of the mutant hemoglobins using recombinant DNA technology that are useful as substitutes for red blood cells.

BACKGROUND OF THE INVENTION

The prevalence of infectious agents such as HIV and hepatitis in red blood cells of human blood products coupled with blood shortages from lack of suitable donors has led to great interest in the development of red cell substitutes, particularly human hemoglobin ("Hb") and its derivatives. Hemoglobin is the oxygen-carrying component of blood, circulated through the blood stream inside erythrocytes (red blood cells).

Human normal adult hemoglobin ("Hb A") is a tetrameric protein containing two α chains having 141 amino acid residues each and two β chains having 146 amino acid residues each, and also bearing prosthetic groups known as hemes. The erythrocytes help maintain hemoglobin in its reduced, functional form. The heme-iron atom is susceptible to oxidation, but may be reduced again by one of two systems within the erythrocyte, the cytochrome $b_5$, and glutathione reduction systems.

The use of cell-free solutions of hemoglobin as a potential oxygen-carrying red cell substitute has been investigated for a long time. See, for example, Mulder, A. G., et al., *J. Cell Comp. Physiol.* 5:383 (1934), the disclosure of which is incorporated herein by reference. The use of unmodified cell-free human hemoglobin purified from red blood cells suffers from several limitations in addition to contamination and supply limitations noted above, namely, an increase in oxygen affinity due to loss of the cofactor 2,3-diphosphoglycerate ("2,3-DPG"), and dissociation of Hb tetramers into αβ dimers which are cleared by renal filtration and which can cause long-term kidney damage. See, for example, Bunn, H. F., et al., *J. Exp. Med.* 129:909 (1969), the disclosure of which is incorporated herein by reference.

Hemoglobin is able to alter its oxygen affinity, thereby increasing the efficiency of oxygen transport in the body due to its dependence on 2,3-DPG, an allosteric regulator. 2,3-DPG is present within erythrocytes at a concentration that facilitates hemoglobin to release bound oxygen to tissues. In the absence of 2,3-DPG, hemoglobin binds oxygen more tightly and does not readily release its bound oxygen. Thus, native human normal adult hemoglobin ("Hb A") were it to be introduced into a subject would not be able to properly allow oxygen to be transported through the body due to a lack of 2,3-DPG in the blood plasma.

Human globins and hemoglobins have been expressed in the following: transgenic mice, see, for example, Chada, K., et al., *Nature (London)* 314:377 (1985) and Townes, T. M., et al.,*EMBO J*. 4:1715 (1985), the disclosures of which are incorporated herein by reference; transgenic swine as described by Swanson, M. E., et al., *Bio/Technology* 10:557 (1992), the disclosure of which is incorporated herein by reference; insect cell cultures as reported by Groebe, D. R., et al., *Protein Expression and Purification* 3:134 (1992), the disclosure of which is incorporated herein by reference; yeast as described by Wagenbach, M., et al., *Bio/Technology* 9:57 (1991) and DeLiano, J. J., et al., *Proc. Natl. Acad. Sci. USA* 90:918 (1993), the disclosures of which are incorporated herein by reference, and *Escherichia coli* ("*E. coli*") as described by Hoffman, S. J., et al., *Proc. Natl. Acad. Sci. USA* 87:8521 (1990), Hernan, R. A., et al., *Biochemistry* 31:8619 (1992), and Shen, T.-J., et al., *Proc. Natl. Acad. Sci. USA* 90:8108 (1993), the disclosures of which are incorporated herein by reference. In many respects, the *E. coli* system is the best choice for such purposes because of its high expression efficiency and the ease of performing site-directed mutagenesis.

The first *E. coli* system to express human α- or β-globin as a fusion protein was developed as described by Nagai, K., et al., *Nature (London)* 309:810 (1984) and Nagai, K., et al., *Methods Enzymol.* 153:461 (1987), the disclosures of which are incorporated herein by reference, but the product processing procedure of this system is very laborious and gives a low yield. Thus, this expression system is not desirable, especially when large amounts of recombinant hemoglobin ("r Hb") are required for biochemical, biophysical, and biological studies.

Hoffman, S. J., et al., *Proc. Natl. Acad. Sci. USA* 87:8521 (1990) have reported a coexpression system in which the synthetic human α- and β-globin genes are organized in a single cistron and are expressed in equal amounts. Both of the expressed α- and β-globins are properly assembled with endogenous hemes into tetrameric Hb molecules in *E. coli*. Hernan, R. A., et al., *Biochemistry* 31:8619 (1992) have reported the expression of a nonfusion single β-globin in *E. coli*. Although these two nonfusion systems work very well in several aspects, an extra methionine residue is retained at the amino (N)-termini of both α- and β-globins.

The natural N-terminal valine residues of Hb A are known to play important roles in regulating oxygen affinity, the Bohr effect, and interactions with allosteric effectors and anions as reported by Bunn, H. F., et al., eds. *Hemoglobin: Molecular, Genetic and Clinical Aspects* (W. B. Saunders, Co., Philadelphia, Pa.) pp. 37–60 (1986), the disclosure of which is incorporated herein by reference. The extra methionine can alter the N-terminal conformation of the Hb molecule as reported by Kavanaugh, J. S., et al., *Biochemistry* 31:8640 (1992), the disclosure of which is incorporated herein by reference. Hence, the oxygenation properties of Hb depend on the integrity of the N-terminal residue thereby mandating the removal of the extra methionine residues from the N-termini of both α- and β-globins of the expressed Hb before the *E. coli* system can be used effectively for the production of desired unmodified and mutant Hbs.

Methionine aminopeptidase ("Met-AP" or "MAP") has been found to be responsible for the removal of the N-terminal methionine residue from a nascent peptide chain in *E. coli*, Salmonella, Bacillus, and yeast, and the Met-APs from a variety of organisms have been purified and characterized. See. for example, Ben-Bassat, A., et al.,*J. Bacteriol.* 169:751 (1987) and U.S. Pat. Nos. 4,865,974, 4,870,017, and 5,013,662, the disclosures of which are incorporated herein by reference. These enzymes possess unique specificity for the N-terminal methionine of a peptide or a protein, and the Met-APs of *E. coli* and *Salmonella typhimurium* have been reported to remove the N-terminal methionine from a number of expressed foreign proteins. Ben-Bassat, A., et al., *J. Bacteriol.* 169:751 (1987).

The cooperative oxygenation of Hb, as measured by the Hill coefficient ("n") is a convenient measure of some of its allosteric properties. See, Dickerson, R. E., et al., *Hemoglobin: Structure, Function, Evolution. and Pathology*, (The Benjamin Cummings Publishing Co., Menlo Park, Calif.) (1983), the disclosure of which is incorporated herein by reference. Hb A has an $n_{max}$ value of approximately 3 in its binding with $O_2$ under usual experimental conditions. Human abnormal Hbs with amino acid substitutions in the $\alpha_1\beta_2$ (or $\alpha_2\beta_1$) subunit interface generally show high oxygen affinity and reduced cooperativity in $O_2$ binding compared to Hb A. See, for example, Dickerson, R. E., et al., Id. (1983); Bunn, H. F., et al., *J. Biol. Chem.* 249:7402 (1974); and Perutz, M. F., et al., *Mechanisms of Cooperativity and Allosteric Regulation in Proteins* Cambridge University Press (1990). Thus, it has been suggested that the $\alpha_1\beta_2$ subunit interface is important for the functional properties of Hb. For example, human mutant Hbs with an amino acid substitution at the β99Asp possess greatly reduced cooperativity and increased oxygen affinity relative to those exhibited by Hb A. Examples of such mutant hemoglobins are Hb Kempsey (β99Asp→Asn) (Reed, C. S., et al. *Blood* 31:623 (1968)); Hb Yakima (β99Asp→His) (Jones, R. T., et al., *J. Clin. Invest.* 46:1840 (1967)); and Hb Radcliff (β99Asp→Ala) (Weatherall, D. J., et al., *British J. Haematol.* 35:177 (1977)), the disclosures of which are all incorporated herein by reference. Fermi, G., et al., *J. Mol. Biol.* 175:159 (1984), the disclosure of which is incorporated herein by reference, have performed X-ray crystallographic studies of deoxy-Hb A (Hb A without oxygen molecules) that show that β99Asp is hydrogen-bonded to both α42Tyr and α97Asn in the $\alpha_1\beta_2$ subunit interface. This suggests that the essential role of β99Asp is to stabilize the deoxy-Hb molecule by making intersubunit hydrogen bonds.

Recently two recombinant Hb ("r Hb") mutants have been constructed involving mutation of α42Tyr which result in very different properties in the resulting mutants. r Hb (α42Tyr→His) of Ishimori, K., et al., *J. Biol. Chem.* 264:14624 (1989) and Imai, K., et al., *J. Mol. Biol.* 218:769 (1991), the disclosures of which are incorporated herein by reference, exhibits some cooperativity in binding oxygen (n=2 at pH 6.8) and moderate oxygen affinity. r Hb (α42Tyr→Phe) (Ishimori, K., et al., *J. Biol. Chem.* 264:14624 (1989) and Imai, K., et al., *J. Mol. Biol.* 218:769 (1991)), the disclosures of which are incorporated herein by reference, exhibits almost no cooperativity in binding oxygen (n=1.2) and possesses very high oxygen affinity. The differences in the properties between these two mutants have been attributed to the presence of a weak hydrogen bond between α42His and β99Asp in the deoxy state of r Hb (α42Tyr→His), but not in deoxy-r Hb (α42Tyr→Phe). It is known that abnormal Hbs with an amino acid substitution at either β99Asp or α42Tyr which lose the intersubunit hydrogen bonds in the deoxy form, also lose their functional properties, therefore it has been suggested that these hydrogen bonds may be crucial for the structure and function of the Hb molecule.

Hb A in its oxy form (Hb A with oxygen molecules) has a characteristic hydrogen bond between α94Asp and β102Asn in the $\alpha_1\beta_2$ subunit interface as reported by Shaanan, B., et al., *J. Mol. Biol.* 171:31 (1983), the disclosure of which is incorporated herein by reference. Human Hbs with an amino acid substitution at either the α94Asp position such as Hb Titusville (α94Asp→Asn) (Schneider, R. G., et al., *Biochim. Biophys. Acta.* 400:365 (1975), the disclosure of which is incorporated herein by reference) or the β102Asn position such as Hb Kansas (β102Asn→Thr) (Bonaventura, J., et al., *J. Biol. Chem.* 243:980 (1968), the disclosure of which is incorporated herein by reference), as well as others, exhibit very low oxygen affinity. However, all these Hb mutants which directly disrupt the hydrogen bond between α94Asp and β102Asn in the oxy form of Hb show greatly reduced cooperativity in the binding of oxygen and additionally dissociate easily into dimers when in the ligated state.

Low oxygen affinity human mutant Hbs which do not involve either α94Asp or β102Asn also exist. For example, Hb Presbyterian (β108Asn→Lys) (Moo-Penn, W. F., et al., *FEBS Lett.* 92:53 (1978) and O'Donnell, J. K., et al.,*J. Biol. Chem.* 269:27692 (1994); Hb Yoshizuka (β108Asn→Asp) (O'Donnell, J. K., et al., *J. Biol. Chem.* 269:27692 (1994) and recombinant Hb Mequon (β41Phe→Tyr) (Baudin, V., et al., *Biochim. Biophys. Acta.* 1159:223 (1992), the disclosures of which are incorporated herein by reference, all exhibit low oxygen affinity compared to Hb A, but they all exhibit a variable amount of cooperativity as measured by the Hill coefficient, with n varying from 1.8 to 2.9.

Molecular dynamics ("MD") simulations have been used to calculate the free energy difference between native and mutant proteins. See, for example, Dang, L. X., et al.,*J. Am. Chem. Soc.* 111:8505 (1989), and Gao, J., et al., *Science* 244:1069 (1989), the disclosures of which are incorporated herein by reference. MD simulations of Hb Radcliff (β99Asp→Ala) show close agreement between the measured thermodynamic value and the calculated value as reported by Gao, J., et al., *Science* 244:1069 (1989). MD simulations have been used to successfully design compensatory amino acid substitutions in an abnormal Hb which restore its allosteric properties as reported by Kim, H.-W., et al., *Proc. Natl. Acad. Sci. USA* 91:11547 (1994), the disclosure of which is incorporated herein by reference.

Shen, T.-J., et al., *Proc. Natl. Acad. Sci. USA* 90:8108 (1993), the disclosure of which is incorporated herein by reference, describe an *E. coli* expression plasmid (pHE2) in which synthetic human α- and β-globin genes are coexpressed with the *E. coli* methionine aminopeptidase gene under the control of separate tac promoters. *E. coli* cells transformed with this plasmid express r Hb A from which the N-terminal methionines have been effectively cleaved by the coexpressed MAP. The resulting recombinant Hb A which lacks an N-terminal methionine is identical to the native Hb A in a number of structural and functional properties.

There remains a need, however, for a mutant hemoglobin species that can be used as a component of a hemoglobin-based blood substitute or therapeutic agent. of particular interest is a mutant hemoglobin that possesses a low oxygen affinity, but high cooperativity in oxygen binding, and which exhibits no unusual subunit dissociation when ligated. There is a further need for such a hemoglobin produced by recombinant methods and an efficient expression system for producing such a mutant hemoglobin in high yield especially for use in a blood substitute product.

SUMMARY OF THE INVENTION

Accordingly, it is a primary object of the present invention to provide a mutant hemoglobin with low oxygen affinity.

Another object of the present invention is to provide a non-naturally occurring mutant hemoglobin with low oxygen affinity.

Another object of the present invention is to provide a low oxygen affinity mutant hemoglobin produced artificially, preferably by recombinant means, that also has the correct heme conformation.

Yet another object of the present invention is to provide a mutant hemoglobin with a low oxygen affinity but high cooperativity in oxygen binding.

Another object of the present invention is to provide a mutant hemoglobin that in a cell-free environment has similar oxygen binding properties as those of human normal adult hemoglobin in red blood cells.

Yet another object of the present invention is to provide an expression system for producing such mutant hemoglobins.

Still another object of the present invention is to provide an artificial hemoglobin for use as a hemoglobin-based red blood substitute or therapeutic agent.

These and other objects of the present invention are achieved by one or more of the following embodiments.

In one aspect, the invention features a non-naturally occuring mutant human hemoglobin wherein the valine residue at position 96 of the α chain is replaced by a tryptophan residue.

In a preferred embodiment, the hemoglobin possesses low oxygen affinity as compared to normal human adult hemoglobin and high cooperativity in oxygen binding and is produced recombinantly.

In another aspect, the invention features a non-naturally occurring low oxygen affinity mutant hemoglobin that has oxygen binding properties comparable to those of human normal adult hemoglobin in the presence of the allosteric effector 2,3-DPG.

In a preferred embodiment, in the mutant hemoglobin the valine residue at position 96 of the α chain is replaced by a tryptophan residue.

Other features and advantages of the invention will be apparent from the following description of the preferred embodiment, and from the claims.

DESCRIPTION OF THE DRAWINGS

FIGS. 3A and 3B are $^1$H-NMR spectra showing ring-current shifted proton resonances of 4% Hbs (α96Val→Trp) derived from pHE202/JM109 and 4% Hb A in the CO forms in 0.1M phosphate in $H_2O$ at pH 7.0 and 29° C.

FIG. 3A shows purified fractions (a, $b_1$, $b_2$) from Mono S column purification in their CO forms. FIG. 3B shows purified r Hbs (α96Val→Trp) from peaks a, $b_1$, and $b_2$ which were converted from the CO form to the $Fe^{+3}$ state, and then back to the CO form.

(FIG. 4B only). FIG. 4A shows hyperfine-shifted $N_δH$ exchangeable proton resonances of the proximal histidine residue; FIG. 4B shows hyperfine-shifted and exchangeable resonances. "Deoxy-r Hb" in FIG. 4B stands for Deoxy-r Hb (α96Val→Trp).

FIGS. 5A and 5B are exchangeable proton resonances of 4% r HbCO (α96Val→Trp) from peak a and of 4% HbCO A, respectively. FIGS. 5C and 5D are ring-current shifted resonances of 4% r HbCO (α96Val→Trp) from peak a, and of 4% HbCO A, respectively.

FIGS. 6A and 6B are exchangeable proton resonances of 4% r HbCO (α96Val→Trp) from peak a, and of 4% HbCO A, respectively.

FIGS. 6C and 6D are ring-current shifted resonances of 4% r HbCO (α96Val→Trp) from peak a and of 4% HbCO A, respectively.

FIG. 7A shows Hb A (○) and purified fractions of r Hbs (α96Val→Trp ) (peaks a (■), $b_1$ (Δ), and $b_2$ (+)) from a Mono S column; FIG. 7B shows Hb A (○) and purified fractions of r Hbs (α96Val→Trp) from a Mono S column (peaks a (■), $b_1$ (Δ), and $b_2$ (+)) which had been converted from the CO form to the $Fe^{+3}$ state and then back to the CO form.

FIG. 8A shows Hb A (○) and Mono S-purified fractions (peaks a (═), $b_1$ (Δ), and $b_2$ (+)); FIG. 8B shows Hb A (○) and purified fractions of r Hbs (α96Val→Trp) from a Mono S column peaks a (═), $b_1$ (Δ), and $b_2$ (+)) which had been converted from the CO form to the $Fe^{+3}$ state and then back to the CO form.

FIGS. 11A and 11B are $^1$H-NMR spectra showing exchangeable proton resonances (FIG. 11A) and ring-current shifted proton resonances (FIG. 11B) of 4% r HbCO (α96Val→Trp) from peak $b_2$ derived from pHE202/JM109, 4% r HbCO (α96Val→Trp) from peak 2 derived from pHE702/JM109 and Hb A, all in the CO form in 0.1M phosphate in $H_2O$ at pH 7.0 and 29° C. Both r Hb (α96Val→Trp) samples had gone through the oxidation-reduction process before carying out the NMR measurements.

DETAILED DESCRIPTION OF THE INVENTION

I. DEFINITIONS

Figure 1:
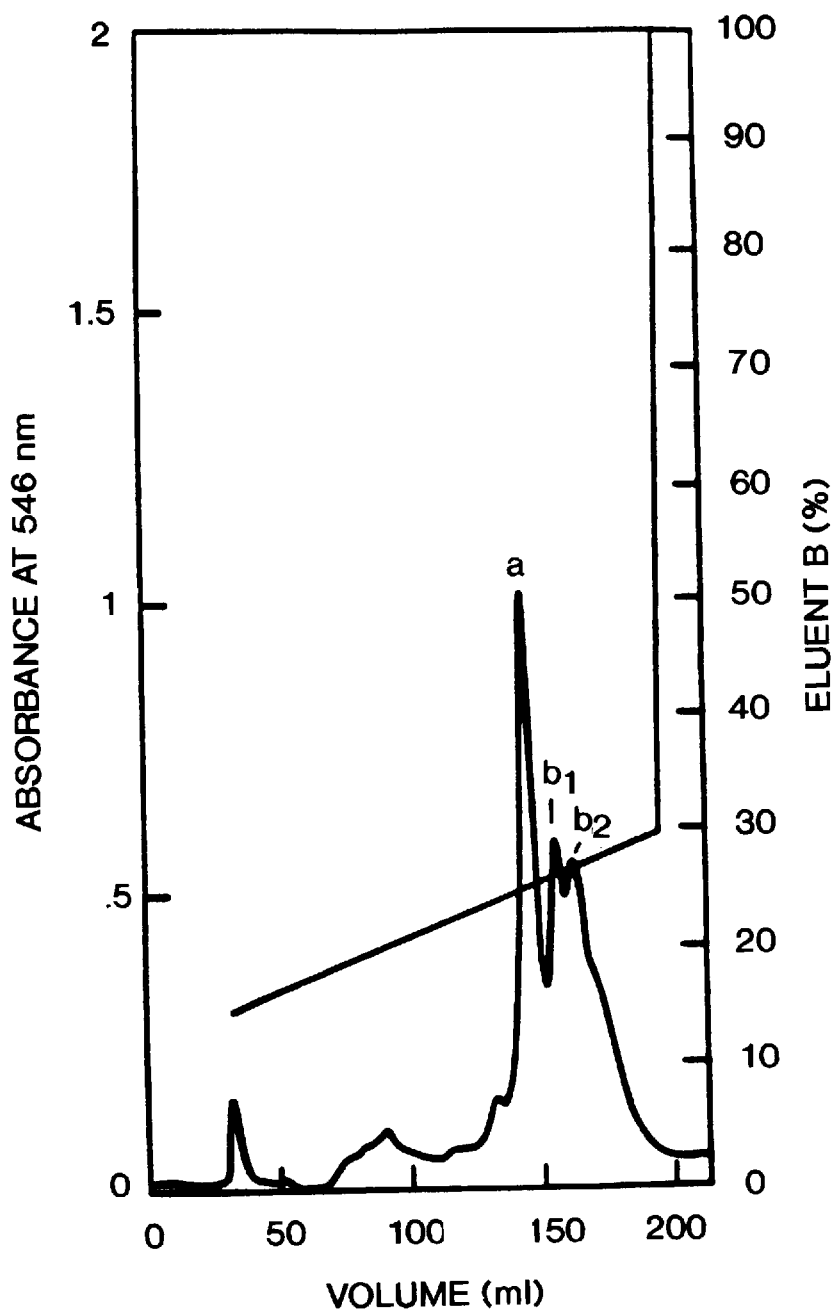
FIG. 1 is a chromatographic elution profile from a Mono S column of r Hb (α96Val→Trp) obtained from the sonicate of *E. coli* JM109 cells that were transformed with plasmid pHE202 ("pHE202/JM109") showing peaks a, $b_1$, and $b_2$. Fractions were monitored at 546 nm.
Figure 2A:
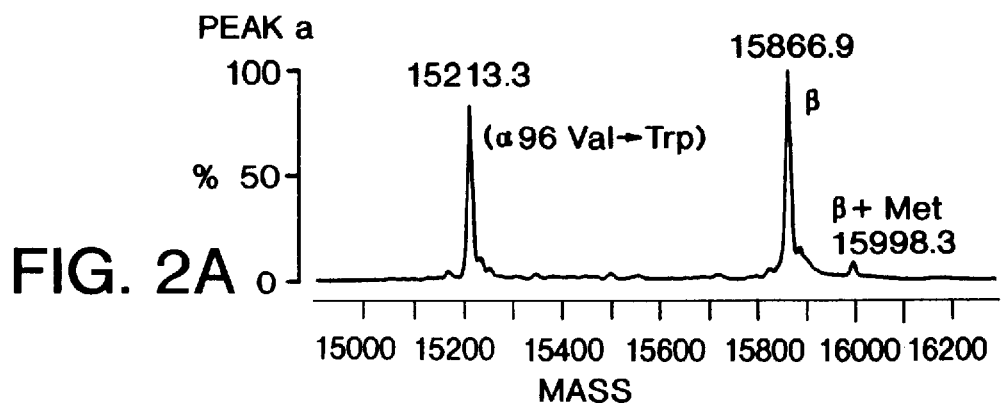
FIGS. 2A–2D are electrospray mass spectra of r Hbs (α96Val→Trp) from peak a (FIG. 2A); peak $b_1$ (FIG. 2B); and peak $b_2$ (FIG. 2C) derived from plasmid pHE202; as well as of Hb A (FIG. 2D) as a reference.
Figure 2B:
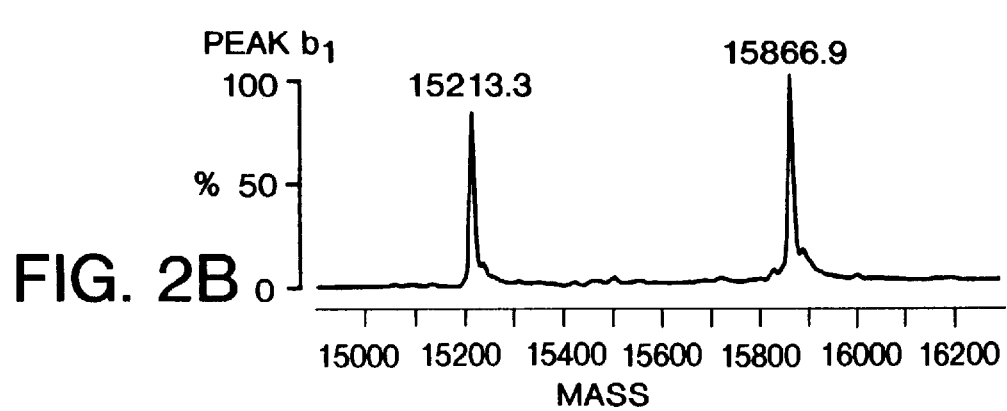
Figure 2C:
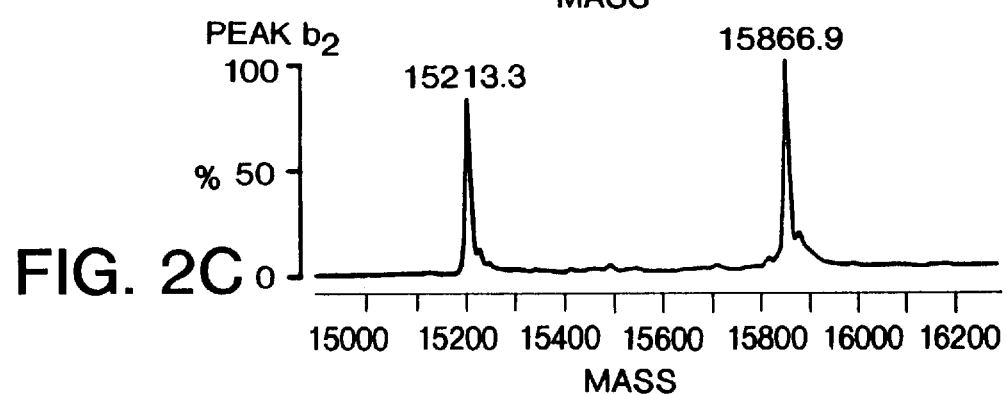
Figure 2D:
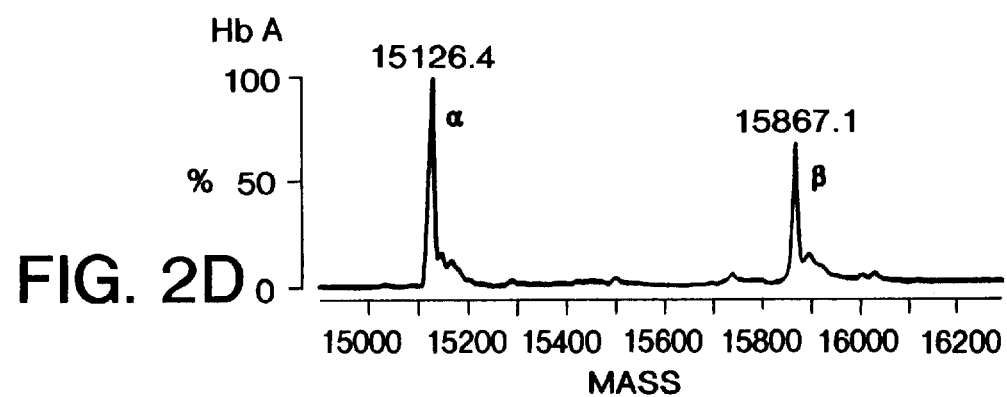

As used herein, "Hb A" or "native Hb A" means human normal adult hemoglobin as obtained from human subjects.

"Recombinant human normal adult hemoglobin," "r Hb A," and "unmodified r Hb A" means human normal adult hemoglobin produced through recombinant DNA technology and having essentially the same structure and function as native Hb A as described by Shen, T.-J., et al., *Proc. Natl. Acad. Sci. USA* 90:8108 (1993).

"r Hb ($\alpha$96Val$\rightarrow$Trp)" refers to a mutant human normal adult hemoglobin produced through recombinant DNA technology in which the valine residue at position 96 of the $\alpha$ chain, located in the $\alpha_1\beta_2$ (or $\alpha_2\beta_1$) interface, has been replaced by a tryptophan residue. This hemoglobin shows a low oxygen affinity but high cooperativity in oxygen binding, and exhibits no unusual subunit dissociation when ligated. "Deoxyl" and "oxy" refer to the oxygenation state of the heme-iron atom in Hb A and r Hb ($\alpha$96Val$\rightarrow$Trp). oxyhemoglobin "Oxy-Hb" or "HbO$_2$" has four oxygen molecules bound to the heme groups; deoxyhemoglobin ("deoxy-Hb") contains no oxygen molecules. In normal arterial blood, normal adult hemoglobin A ("Hb A") is in the oxy form ("oxy-Hb A"). In venous blood, a portion of Hb A is in the deoxy form ("deoxy-Hb A").

"Carbonmonoxy-Hb" "HbCO A," "r HbCO ($\alpha$96Val$\rightarrow$Trp)" and "CO form" all refer to hemoglobin bound to carbon monoxide molecules rather than oxygen molecules.

"Ferri-hemoglobin," "ferri-Hb," "ferric form" "methemoglobin," "met-Hb", and "Fe$^{+3}$ state" all refer to Hb A and r Hb ($\alpha$96Val$\rightarrow$Trp) with their respective heme-iron atoms oxidized to the ferric (Fe$^{3+}$) state. Ferri-Hb does not bind oxygen.

"Ferro-hemoglobin," "ferro-Hb," "Fe$^{+2}$ state", and "ferrous form" refer to Hb A, r Hb ($\alpha$96Val$\rightarrow$Trp), HbCO A, and r HbCO ($\alpha$96Val$\rightarrow$Trp) with their respective heme-iron atoms in the native, reduced ferrous (Fe$^{+2}$) state. Ferro-Hb is capable of binding oxygen or carbon monoxide.

"Control" means a gene coding sequence being subject to another gene in the control region of a DNA molecule, in particular, a promoter, whereby the coding sequence can be expressed and regulated under the control of the promoter. Absent such control, the coding sequences may be expressed at too high or too low a level in the host organism, or at an improper time.

"Met-aminopeptidase," "Met-AP," and "MAP" refer to the enzyme methionine aminopeptidase which specifically cleaves the amino-(N) terminal methionine residue from a peptide sequence.

"Quaternary structural transition" means the structural rearrangement in the subunit interfaces of hemoglobin, such as $\alpha_1\beta_2$ upon going from the deoxy form to the oxy form.

"Oxygen affinity" means the strength of binding of oxygen to a hemoglobin molecule. High oxygen affinity means hemoglobin does not readily release its bound oxygen molecules. The $P_{50}$ is a measure of oxygen affinity.

"Cooperativity" refers to the sigmoidal oxygen-binding curve of hemoglobin, i.e., the binding of the first oxygen to one subunit within the tetrameric hemoglobin molecule enhances the binding of oxygen molecules to other unligated subunits. It is conveniently measured by the Hill coefficient ($n_{max}$). For Hb A, $n_{max}$=3.0.

R-type or R-like and T-type or T-like structures of hemoglobin refer to those hemoglobins which exhibit characteristic quaternary structural markers, such as the proton resonance at 10.7 ppm from DSS as the R-structural marker and the proton resonance at 14 ppm from DSS as the T-structural marker. Some mutant and chemically modified Hbs could have a T- or R- quaternary structural marker but with altered tertiary structures.

II. METHODS AND RESULTS

According to the present invention, a non-naturally occurring low oxygen affinity mutant human hemoglobin is provided as well as means for producing such hemoglobin recombinantly. More particularly, the present invention is directed to a recombinantly produced mutant of Hb A, denoted r Hb ($\alpha$96Val$\rightarrow$Trp) herein, in which the valine residue at position 96 of the $\alpha$ chain, located in the $\alpha_1\beta_2$ (or $\alpha_2\beta_1$) subunit interface region, has been replaced by a tryptophan residue respectively, SEQ ID NOS: 1–2; human $\beta$-globin cDNA coding sequence and amino acid sequence, respectively, SEQ ID NOS: 3–4). This new artificial hemoglobin, i.e., derived entirely from sources other than blood, shows a low oxygen affinity but high cooperativity in oxygen binding. Further, it exhibits no unusual subunit dissociation when ligated. In a cell-free environment, the r Hb ($\alpha$96Val$\rightarrow$Trp) of the present invention has similar oxygen binding properties as those of Hb A in red blood cells. Such a low oxygen affinity hemoglobin mutant produced recombinantly is of value as a component of a hemoglobin-based blood substitute. Such a mutant is also useful in radiation treatments of tumors, trauma, and hemodilution in surgery.

It is also within the scope of the present invention to prepare and use other low oxygen affinity hemoglobins with other appropriate mutations. In particular, the methods of the present invention may be used to produce other mutant hemoglobins with additional advantageous properties. It is believed that other mutations in the $\alpha_1\beta_2$ interface and the central cavity of hemoglobin may yield other useful low oxygen affinity mutants. Methods for evaluating suitability of such mutants for use in a blood substitute or therapy are described herein below.

Molecular dynamics simulations detailed below suggest that the unique oxygen-binding property of r Hb ($\alpha$96Val$\rightarrow$Trp) of the present invention may be due to an extra hydrogen bond between $\alpha$96Trp and $\beta$99Asp in the $\alpha_1\beta_2$ subunit interface in the deoxy form of r Hb ($\alpha$96Val$\rightarrow$Trp).

Despite the replacement of a small amino acid residue, valine, by a large tryptophan residue in the $\alpha_1\beta_2$ subunit interface, it is shown below that this artificial hemoglobin shows very similar tertiary structure around the heme pockets and quaternary structure in the $\alpha_1\beta_2$ subunit interface compared to those of human normal adult hemoglobin. The tertiary structure of the hemoglobin molecule refers to the steric relationships of amino acid residues that are far apart in the linear chain sequence that cause each chain to fold upon itself, while the quaternary structure refers to how the subunit chains may interact with each other.

As will be demonstrated below, the artificial hemoglobin of the present invention possesses the property that the ligated form of this hemoglobin, for example, the carbonmonoxy form, in the oxy-(R-) type quaternary structure, can be converted to the deoxy-(T-) type quaternary structure without changing the ligation state by the addition of an allosteric effector, such as inositol hexaphosphate. This conversion can also be carried out by lowering the temperature in the absence of inositol hexaphosphate. The recombinant hemoglobin of the present invention can therefore be used to gain new insights regarding the nature of subunit interactions in the $\alpha_1\beta_2$ interface and the molecular basis for the allosteric mechanism of hemoglobin.

Clearly, the methods of the present invention may also be used to produce other mutant artificial hemoglobins with different properties as well as hemoglobins with mutations that compensate for mutants that are naturally occurring. The preferred materials and methods for obtaining r Hb (α96Val→Trp) are given in the following reference example. While the r Hb (α96Val→Trp) of the present invention is preferably produced recombinantly, it is understood that non-recombinant methods may also be used.

REFERENCE EXAMPLE

A. Plasmid DHE202

Construction of Expression Plasmid pHE202

Two plasmids that express r Hb (α96Val→Trp) have been constructed in accordance with the present invention, plasmid pHE202 and plasmid pHE702. The protocols and results for plasmid PHE202 appear first as follows.

The Hb A expression plasmid pHE2 containing synthetic human α- and β- globin genes was used as a starting plasmid. The construction of plasmid pHE2 and properties of the r Hb A produced are fully described in Shen, T.-J., et al., *Proc. Natl. Acad. Sci. USA* 90:8108 (1993), the disclosure of which is incorporated by reference. In constructing plasmid pHE2, the synthetic human α- and β- globin genes were obtained from plasmid pDLIII-13e (a gift from Somatogen, Inc., Boulder Colo., and fully disclosed in Hoffman, S. J., et al., *Proc. Natl. Acad. Sci. USA* 87:8521 (1993), the disclosure of which is incorporated herein by reference). The coding sequence of the *E. coli* Met-AP gene was obtained from plasmid pSYC1174 (pSYC1174 in *E. coli* MM294 was gift from Cetus Corp., Emeryville, Calif.), and this strain was also deposited with the American Type Culture Collection under accession number ATCC 53245 and is available to the public. See also, U.S. Pat. Nos. 4,865,974, 4,870,017 and 5,013,662. Plasmid pHE2 coexpresses the synthetic human α- and β-globin genes with the *E. coli* Met-AP gene under the control of separate tac promoters.

Site-directed mutagenesis was then carried out to replace the valine residue at position 96 of the α chain by a tryptophan residue as follows. The synthetic human α- and β-globin genes (from plasmid pDLIII-13e) was inserted into phagemid pTZ18U (Bio-Rad Laboratories, Hercules, Calif.) by methods well known in the art. A synthetic oligonucleotide of sequence 5'-TTTGAAGTTCCATG-GATCAAC-3' (SEQ. ID NO:15 mutated codon is underlined) was synthesized at the DNA Synthesizing Facility, University of Pittsburgh, and used as a primer to introduce the mutation, α96Val→Trp, by standard DNA synthesis methodology. Techniques for oligonucleuticle synthesis are well known and this invention is not limited to any particular technique. Site-directed mutagenesis was performed as described by Kunkel, T. M., et al., *Proc. Natl. Acad. Sci. USA* 82:488 (1985) and Shen, T.-J., et al., *Proc. Natl. Acad. Sci. USA* 90:8108 (1993), the disclosures of which are incorporated herein by reference. The human normal α-globin gene in plasmid pHE2 was then replaced with the mutated gene to produce plasmid pHE202. Plasmid pHE202 in host cell *E. coli* JM109 and designated pHE202/JM109 was deposited with the American Type Culture Collection of Rockville, Md. on Apr. 26, 1995 under number ATCC 69792.

Growth of Cells Plasmid pHE202 was transformed into *E. coli* JM109 cells (Promega, Madison, Wis.) by methods well known in the art. The cells were grown in TB medium which contains 1.2% bactotryptone, 2.4% bactoyeast extract, 0.4% glycerol, 17 mM $KH_2PO_4$, 72 mM $K_2HPO_4$, and 100 μg ampicillin (Sigma, St. Louis, Mo.) in a 20-liter Microferm Model MF20 fermentor (New Brunswick Scientific, Edison, N.J.) at 30° C. until the cell density reached $1-2\times10^9$ cells per ml.

The expression of r Hb (α96Val→Trp) was induced by adding isopropyl β-thiogalactopyranoside to a concentration of 0.2 mM. The culture was then supplemented with hemin (20 mg/liter) (Sigma, St. Louis, Mo.) and glucose (10 g/liter) and the growth was continued for at least another four hours. The cells were then harvested by centrifugation and stored frozen in 100-gram portions at −80° C. until needed for further purification.

Although *E. coli* cells are presently preferred for expressing and producing the recombinant mutant hemoglobin of the present invention, the invention is not limited to *E. coli* cells. Other appropriate expression systems such as yeast, insect cells and transgenic animals such as pigs and cows may also advantageously be used to express mutant hemoglobins. Plasmid pHE202 has been Boptimized for *E. coli* cells whereas pHE702, described in detail below, was constructed from human genes and thus other expression systems may be advantageously used with human genes as contained in plasmid pHE702.

Isolation and Purification of Recombinant Hbs

The r Hb (α96Val→Trp) obtained from cells transformed with plasmid pHE202 was purified as essentially described by Shen, T.-J., et al., *Proc. Natl. Acad. Sci. USA* 90:8108 (1993), with minor modifications.

The frozen stored cell paste was put into lysis buffer (40 mM Tris-base/1 mM benzamidine (Sigma) at 3 ml/gm of cell paste) and stirred until it was completely suspended. Lysozyme (Sigma) (1 mg/g cell paste), dissolved in 10 ml of 40 mM Tris-HCl pH 8.0, was added to the cell suspension and allowed to stand at 4° C. for about 45 minutes (solution becomes very viscous). $MgCl_2$ and $MnCl_2$ were added to a final concentration of 10 mM and 1 mM, respectively. About 3–5 μg/ml of DNAse (ICN Biochemical, Inc., Costa Mesa, Calif.) was added and stirred for 30–60 minutes or until viscosity drops. The lysate was then sonicated in a Branson 450 sonifier (Branson, Danbury, Conn.) in an ice bath at 65–75 W in three 3-minute cycles stopping between cycles to ensure the lysate was kept cold. The lysate was then centrifuged at 4° C. for 45 minutes at 14,000 rpm in a Sorvall GSA rotor (E. I. dupont, Wilmington, Del.). The supernatant was then saturated with CO gas and allowed to stand at 4° C. for 3–4 days. The pH of the supernatant was adjusted to 8.0 with 1M Tris base and 10% polyethyleneimine (Sigma) (vol/vol) was added slowly to a final concentration of 0.5% in order to precipitate out the nucleic acids. This was stirred under CO gas for 15 minutes and then centrifiged at 14,000 rpm as above. The pH of the supernatant was adjusted to 8.3 with 1M Tris base and put through a Millipore Minitan Acrylic Ultrafiltration System (Millipore Corp., Bedford, Mass.) until the volume was around 150 ml. The concentrated solution was dialyzed against 20 mM Tris-HCl/0.1 mM triethylenetetraamine ("TETA") pH 8.3 (referred to below as "Q2 buffer") overnight with a change of buffer. The pH and conductivity were adjusted so that they were the same as Q2 buffer, usually by adding 20 mM Tris-base/0.1 mM TETA.

Two columns were used in the final purification process using a Pharmacia fast protein liquid chromatography ("FPLC") system (Pharmacia Biotech, Inc., Piscataway, N.J.). The first column used was a Q-Sepharose fast-flow column (Pharmacia anion exchanger) (5 cm×28 cm) which was used to bind Hb. After loading the sample onto the column, it was washed with Q2 buffer (20 mM Tris HCl/0.1 mM TETA, pH 8.3) and monitored at 260 nm until the contaminating nucleic acids had eluted. The Hb fraction was then eluted from the column with 20 mM Tris-HCl at pH 7.2. The eluent was concentrated with 10 mM phosphate/0.1 mM ethylenediaminetetraacetic acid ("EDTA"), pH 6.8 (Buffer A). The second column employed was a Mono S column (Pharmacia cation exchanger, HR6/10). The equilibrated sample was purified on the Mono S column by running a gradient from 10 mM sodium phosphate/0.1 mM ethylenediaminetetraacetic acid ("EDTA"), pH 6.8 (Buffer A), to 20 mM sodium phosphate/0.1 mM EDTA, pH 8.3 (Buffer B). Fractions were monitored at 546 nm.

r Hb ($\alpha$96Val→Trp) was eluted in two major peaks as shown in FIG. 1, a symmetrical peak (peak a) followed by two overlapping peaks (peaks $b_1$, and $b_2$). These peaks obtained as described above are referred to hereafter as "peak a", "peak $b_1$", and "peak $b_2$", as further shown in FIG. 1. The Hb concentration was determined by using published extinction coefficients as described by Antonini, E., et al., *Hemoglobin and Myoglobin in Their Reactions with Ligands* (North Holland, Amsterdam) p. 19 (1971), the disclosure of which is incorporated herein by reference.

Forms of Hb

The CO forms of Hbs (e.g., Hb A and r Hb ($\alpha$96Val→Trp)) were prepared by passing a stream of CO gas through a $HbO_2$ or deoxy-Hb solution contained in a flask. This procedure was carried out inside a ventilated fume hood. Deoxy-Hb was usually prepared by converting HbCO or $HbO_2$ to the deoxygenated form in a rotary evaporator under $N_2$ gas at 4° C. as fully disclosed in Lindstrom, T. R., et al., *Proc. Natl. Acad. Sci. USA* 69:1707 (1972). Oxy-Hb was prepared by exposing deoxy-Hb solution to air or $O_2$ gas.

Protein Sequencing

Automated cycles of Edman degradation were performed with an Applied Biosystem gas/liquid-phase sequencer (Model 470/900A) that was equipped with an on-line phenylthiohydantoin-amino acid analyzer (Model 120A) as described by Hewick, R. M., et al., *J. Biol. Chem.* 256:7990 (1981), the disclosure of which is incorporated herein by reference.

Mass Spectrometry

Hb samples subjected to mass spectrometry were dialyzed extensively against distilled $H_2O$ and then lyophilized. Immediately before analysis, the samples were dissolved in water to a concentration of 125 pmol of Hb per $\mu$l of $H_2O$ (7.8 mg/ml). Aliquots of these solutions were then diluted to give a final concentration of 10 pmol/$\mu$l of 50:50 water/acetonitrile containing 0.2% formic acid. Aliquots (10 $\mu$l) of these final solutions were introduced into the electrospray ion source at 5 $\mu$l/minute.

The electrospray analyses were performed on a VG Quattro-BQ (Fisons Instruments, VG Biotech, Altrincham, U.K.), a triple quadrupole instrument with a mass range for singly charged ions of 4000. Scanning was performed from m/z 980 to 1400 in 10 seconds per scan. The data obtained from 20 scans were summed to give the final spectra. Mass scale calibration used the multiply charged ion peaks from the $\alpha$ chain ($M_r$=15,126.4) of Hb A as an external reference. The molecular weights calculated from the amino acid sequences of normal $\alpha$ chain and normal $\beta$ chain are 15,126.4 and 15,867.2, respectively. Such values are based on the following atomic weights of the elements: C=12.011; H=1.00794; N=14.00674; O=15.9994; and S=32.066, as reported by Commission on Atomic Weights and Isotopic Abundances, *Pure Appl. Chem.* 63:975 (1991), the disclosure of which is incorporated herein by reference. The resulting electrospray mass spectra are shown in FIGS. 2A–2D.

Conversion of Oxidation State of the Heme-Iron Atoms

In order to oxidize Hbs, in this case the CO form of Hb A and r Hb ($\alpha$96Val→Trp), to the $Fe^{+3}$ state, the concentration of Hb solution in 0.1M phosphate at pH 6.5 was determined. A 3-molar excess of $K_3Fe(CN)_6$ (Fisher Scientific) or other suitable oxidizing agent was added and the solution was stirred at room temperature for 1 hour. During this time, the Hb solution changed from red to brownish color. The resulting oxidized Hb ($Fe^{+3}$) was put through a Sephadex G-25 (medium) column (Sigma) using 0.1M phosphate at pH 6.5 to remove excess $K_3Fe(CN)_6$ and was left to stand overnight at room temperature.

The oxidized Hb ($Fe^{+3}$) was subsequently reduced by first preparing 0.1M phosphate at about pH 7.0 in a test tube, and deoxygenating the buffer by bubbling nitrogen through the buffer to remove the dissolved oxygen. In another tube, enough sodium dithionite (Fluka Chemie, Switzerland) was weighed out to give a 0.1M solution of dithionite. The tube was then flushed with nitrogen to remove oxygen. The deoxy phosphate buffer was then anaerobically transferred to the deoxy dithionite to give a 0.1M final concentration. A stream of CO was blown across the top of (not bubbled through) the oxidized Hb solution. The deoxy dithionite buffer solution was added to the oxidized Hb solution until the color changed back to bright red. At this point, the optical spectrum can be checked to ensure all the Hb ($Fe^{+3}$) is reduced to Hb ($Fe^{+2}$). A Sephadex G-25 column was equilibrated with the same CO gassed buffer that was used for reducing the Hb. The reduced Hb solution was then put through the Sephadex G-25 column using the same CO gassed buffer. The resulting oxidized/reduced Hb was then preferably purified through an FPLC Mono S column as described above. The resulting oxidized, reduced, Mono S-purified r Hb ($\alpha$96Val→Trp) or Hb A was then converted to the carbonmonoxy or oxy form as desired as described above.

Other suitable oxidizing agents may be used to oxidize ferro-hemoglobin ($Fe^{+2}$) to ferri-Hb ($Fe^{+3}$) such as, for example, ferricyanide, copper, hydrogen peroxide, hydroxylamine, nitrites, hydrazines, thiols, arylamines or any compound with an electrical chemical potential ("$E_m$") greater than 0.14 volt. Other suitable reducing agents that may be used to reduce ferri-Hb ($Fe^{+3}$) to ferro-hemoglobin ($Fe^{+2}$) are: (i) for non-enzymatic reduction-dithionite, metabisulfite, cysteine, reduced glutathione, and ascorbic acid (in the presence of methylene blue); and (ii) for enzymatic reduction-cytochrome $b_5$ reductase, NADPH-flavin reductase, and any other compound with an $E_m$ less than 0.14 volt may be used. See, Bunn, H. F., et al., *Hemoglobin: Molecular, Genetic and Clinical Aspects* (W. P. Saunders, Inc., Philadelphia, Pa.) pp. 634–662 (1986), the disclosure of which is incorporated herein by reference.

NMR Measurements $^1$H-NMR spectroscopy has been shown to be an excellent tool to investigate the structural features of Hb A such as the tertiary structure, including the heme pockets, and the quaternary structure, namely, the subunit interfaces. See, Ho, C., *Adv. Protein Chem.* 43:153 (1992), the disclosure of which is incorporated herein by reference. The ring-current shifted $^1$H resonances of hemoglobin are known to be sensitive to the heme orientation and environment of r Hb A in the CO form (Ho, C., *Adanc. Protein Chem.* 43:153 (1992) and Shen, T.-J., et al., *proc. Natl. Acad. Sci. USA* 90:8108 (1993), the disclosures of which are incorporated herein by reference).

$^1$H-NMR spectra were obtained on a Bruker AM-300 spectrometer that was operated at 300 MHz and at temperatures ranging from 10° C.–36° C. All of the Hb samples were placed in 0.1M sodium phosphate buffer (in 100% $H_2O$) at pH 7.0. The Hb concentration range was approximately 4%.

The water signal was suppressed by using the "jump-and-return" pulse sequence as reported by Plateau, P., et al., *J. Am. Chem. Soc.* 104:7310 (1982), the disclosure of which is incorporated herein by reference. The $^1$H-NMR spectra of the particular carbonmonoxy-Hb ("HbCO") and deoxy-Hb samples were obtained by using the proton decoupling coil of a 5-mm multinuclear probe (Bruker) with 90° pulses of 9.7 μseconds, spectral widths of 8 kHz (16 kHz for deoxy-Hb), and 8000-data points. Typically, 256 or 1024 scans were averaged to improve the signal-to-noise ratio. Proton chemical shifts are referenced to the methyl proton resonance of the sodium salt of 2,2-dimethyl-2-silapentane-5 sulfonate ("DSS") indirectly by using the water signal, which signal occurs at 4.76 ppm downfield from that of DSS at 29° C., as the internal reference. The resulting $^1$H-NMR spectra are shown in FIGS. 3–6 and 11.

Oxyqen Binding of Hb A Samples oxygen-dissociation curves were measured by a Hemox-Analyzer (TCS Medical Products, Huntington Valley, Pa.) from 16°–37° C. in 0.1M sodium phosphate buffer in the pH range of 6.0–8.3. The methemoglobin reductase system, described by Hayashi, A., et al., *Biochim. Biophys. Acta* 310:309 (1973), the disclosure of which is incorporated herein by reference, was added (30–60 μl) to prevent the formation of ferri-Hb. Partial pressure at 50% oxygenation ($P_{50}$) and the Hill coefficient ($n_{max}$) were determined from each curve. The results of these studies are shown in FIGS. 7–10.

MD Simulations

MD simulations were carried out using the stochastic boundary method of Brooks, C. L., et al., *J. Mol. Biol.* 208:159 (1989), the disclosure of which is incorporated herein by reference, using CHARMM22 (Brooks, B. R., et al., *J. Comp. Chem.* 4:187 (1983), the disclosure of which is incorporated herein by reference) with standard parameters for the polar hydrogen protein model (param 19).

For a comparison of the stability of different hemoglobin conformations, the molecule was partitioned into MD and Langevin regions with radii of 10 angstroms and 15 angstroms, respectively, which were centered on the reference coordinates of the crystal structure of deoxy-Hb A as given by Fermi, G., et al., *J. Mol. Biol.* 175:159 (1984), the disclosure of which is incorporated herein by reference. These coordinates refer to roughly in the middle of the $C_\beta$ of the two α96Val side chains. For the calculation of the free energy of simulation, the molecule was partitioned into MD and Langevin regions with radii of 10 angstroms and 15 angstroms, respectively, which were centered on the center-of-mass coordinates of the $C_\beta$ of the β99Asp side chain in the deoxy (Fermi, G., et al., *J. Mol. Biol.* 175:159 1984) and oxy crystal structures (Shannan, B., *J. Mol. Biol.* 171:31 (1983)), the disclosure of which is incorporated herein by reference) of Hb A. The inside sphere was filled with charm-adapted pre-equilibrated TIP3P water molecules as described by Jorgensen, W. L., et al., *J. Chem. Phys.* 79:926 (1983), the disclosure of which is incorporated herein by reference. The deoxy simulation included 103 water molecules, and the oxy simulation included 83 water molecules.

Because there is no available crystal structure for Hb (α96Val→Trp), several different local conformations for α96Trp were considered for the initial conformation. Four possible side-chain angles of tryptophan from the rotamer library (Ponder, J. W., et al., *J. Mol. Biol.* 193:775 (1987), the disclosure of which is incorporated herein by reference), which show more than 10% incidence [$\chi_1$=−70.4, $\chi_2$=−100.5 (37.9%); $\chi_1$=64.8, $\chi_2$=−88.9 (20.7%); $\chi_1$=−177.3, $\chi_2$=−95.1 (13.8%); $\chi_1$=−179.5, $\chi_2$=87.5 (10.3%)] were used as the initial orientations for MD simulations. The same number of protein atoms and water molecules were used for each conformation.

The transformation between wild-type and mutant proteins can be achieved by using a hybrid potential function $V_\lambda=(1-\lambda)V_A+\lambda V_B$ (Gao, J., et al., *Science* 244:1069 (1989) and Tidor, B., et al., *Biochemistry* 30:3217 (1991), the disclosures of which are incorporated herein by reference), where λ is a coupling factor between 0 and 1. $V_A$ and $V_B$ are potential energy functions for Hb A and for mutant Hb, respectively. Simulations were done at nine values of $\lambda_i$ (λ=0.1, 0.2, ... 0.9), with 5-ps of equilibration followed by 5-ps of production dynamics, except at λ=0.1 and λ=0.9, where 10-ps of equilibration was employed. Non-bonded interactions were truncated to zero at 8.5 Å and a constant dielectric (ε=1) was used. All bonds involving hydrogen atoms were constrained with the SHAKE algorithm of Ryckaert, J.-P., et al., *J. Comput. Phys.* 23:327 (1977), the disclosure of which is incorporated herein by reference. A 10-ps simulation takes about 2 hours on a SunSparc Workstation 10 with 1-fs integration time.

The free energy of simulations can be obtained from the trajectory files of MD simulations for both deoxy and oxy forms of Hb using the thermodynamic integration method described by Kirkwood, J. G., *J. Chem. Phys.* 3:300 (1935), the disclosure of which is incorporated herein by reference, with the following equation:

$$\Delta G = G_B - G_A$$

$$= \int_0^1 <\Delta V>_\lambda d\lambda \approx \sum_i <\Delta V>_{\lambda_i} \Delta\lambda$$

where $\Delta V = V_B - V_A$, and the thermodynamic average $<\Delta V>_\lambda$ indicates the average of $V_\lambda$ over the hybrid system. The linear form of the thermodynamic equations shows that the total free energy of the simulations can be decomposed into individual additive contributions. The change in the free energy of cooperativity resulting from the mutations can be indirectly obtained from the thermodynamic cycle as shown previously by Gao, J., et al., *Science* 244:1069 (1989).

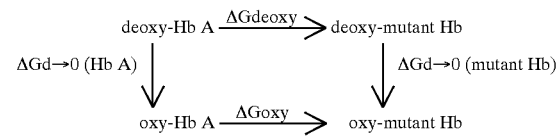

For the purpose of structural analysis carried out, average structures for wild-type (λ=0) and mutant systems (λ=1) were calculated from the nearest states that were simulated (λ=0.1 and λ=0.9, respectively) by using the exponential formulas of Brooks, C. L., et al., *P. Phys. Chem.* 90:6680 (1986), the disclosure of which is incorporated herein by reference:

$$X_0 = \frac{<Xe^{+0.1\beta\Delta v}>_{\lambda=0.1}}{<e^{+0.1\beta\Delta v}>_{\lambda=0.1}}$$

and $$X_1 = \frac{<Xe^{-0.1\beta\Delta v}>_{\lambda=0.9}}{<e^{-0.1\beta\Delta v}>_{\lambda=0.9}}$$

where X represents the Cartesian coordinates of the system, $X_0$ and $X_1$ are the simulation-average wild-type and mutant coordinates, respectively, $\beta=1/k_B T$, and $<>_\lambda$ is an ensemble average under the potential $V_\lambda$.

B. RESULTS

Biochemical Properties of r Hb (α96Val→Trp)

As stated above, the Mono S chromatography of the expressed r Hb (α96Val→Trp) from the sonicated cells of *E. coli* JM109 which harbors plasmid pHE202 resulted in two major peaks (peaks a and b) on Mono S column chromatography as shown in FIG. 1. A symmetrical peak comes out first (peak a) followed by two overlapping peaks (peaks $b_1$, and $b_2$). The peaks so obtained by Mono S chromatography are hereinafter referred to as "peak a", "peak $b_1$", and "peak $b_2$". All of these peaks in the CO form show a visible optical spectrum over the range of 350–700 nm identical to that of Hb A (results not shown).

The electrospray mass spectrometry that was carried out as described above shows that the amino-terminal methionine residues of all three peaks have been effectively cleaved by the coexpressed Met-AP as shown in FIG. 2. For peak a, at least 98% of the α chain has mass 15,213, which is the calculated value for the replacement of a valine residue by a tryptophan residue, and up to about 90% of the β chain has mass 15,867, which is the calculated mass of the β chain of Hb A. There is a small component (<10%) whose mass (15,998) corresponds to that of the normal β chain plus a methionine residue. However, for peaks $b_1$ and $b_2$, both α and β chains have the correct masses with undetectable (<2%) N-terminal methionine.

$^1$H-NMR Studies of r Hb (α96Val→Trp)

i. Conversion of the CO Form to the Ferric Form and Then Back to the CO Form of Hb A comparison of the ring-current shifted $^1$H resonances of all three peaks (a, $b_1$, and $b_2$) of Mono S-purified r Hbs (α96Val→Trp), derived from pHE202/JM109, in their respective CO forms and HbCO A are shown in FIG. 3A. The spectra were obtained using 4% r Hbs (α96Val→Trp) and 4% Hb A in 0.1M phosphate in $H_2O$ at pH 7.0 and at 29° C. converted to their respective CO forms as described above. To obtain the spectra of FIG. 3B, all the hemoglobins were converted from their CO forms to the $Fe^{+3}$ states and back to the CO forms. The $^1$H resonances from 0 to -2.0 ppm from DSS arise from some of the protons of the amino acid residues located in the vicinity of the heme pockets of the Hb molecule and of the porphyrins (Ho, C., *Advanc. Protein Chem.* 43:153 (1992), the disclosure of which is incorporated herein by reference). As can be seen in FIG. 3A, the ring-current shifted $^1$H resonances of r HbCO (α96Val→Trp) from peaks a, $b_1$, and $b_2$ are all somewhat different from those of HbCO A. Also, there are additional resonances which are not seen in HbCO A as well as changes in the intensities in several resonances over the region from 0 to -1.1 ppm from DSS. However, the resonances from -1.7 to -1.8 ppm, which have been assigned to the $γ_2$-methyl groups of the E11Val (distal valine) of the α and β chains of HbCO A (Lindstrom, T. R., et al., *Biochemistry* 11:1677 (1972) and Dalvit, C., et al. *Biochemistry* 24:3398 (1985), the disclosures of which are incorporated herein by reference) from peak a are essentially the same as those of Hb A, while the resonances from peaks $b_1$ and $b_2$ are much broader.

The phenomenon of proper insertion of hemes into the expressed globins using Hb expression plasmid pHE2 in *E. coli* was discussed in Shen, T.-J., et al., *Proc. Natl. Acad. Sci. USA* 90:8108 (1993). They described a conversion of the heme pockets of one of the purification components of r Hb A to those of native Hb A by an oxidation and reduction process. Similarly, the possibility of converting the abnormal $^1$H resonances of r Hb (α96Val→Trp) to those of the native form of hemoglobin was also investigated in the present invention. r Hbs (α96Val→Trp) from all three peaks were first oxidized to their respective ferric states and then reduced back to their respective CO or oxy form as described above. As shown in FIG. 3B, such "converted Hbs" from all three peaks after the oxidation and reduction processes show identical NMR spectra (environments of respective distal valines the same), which are similar to those of r Hb (α96Val→Trp) from peak a before the conversion (FIG. 3A). This suggests that peak a of r Hb (α96Val→Trp) has the correct heme conformation and subunit interface. r Hb (α96Val→Trp) from peak a was therefore used for all further work described herein, unless otherwise specified.

ii. Heme Environment and Subunit Interface

Figure 4A:
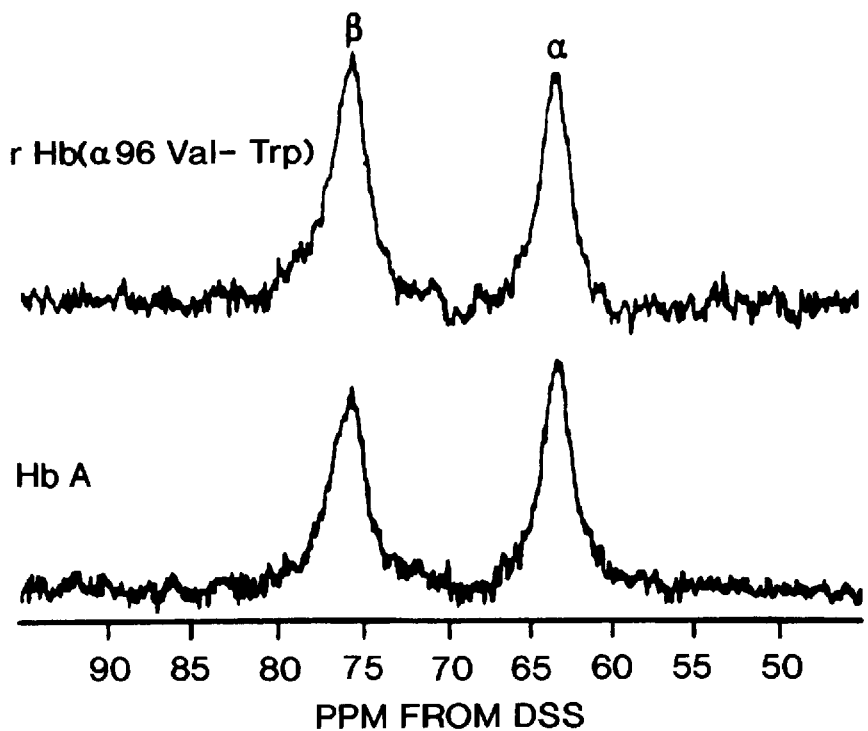
FIGS. 4A and 4B show $^1$H-NMR resonances of 4% r Hb (α96Val→Trp) from peak a derived from pHE202/JM109 and 4% Hb A in their deoxy forms in 0.1M phosphate in $H_2O$ at pH 7.0 and 29° C. (both figures) and 36° C.
Figure 4B:
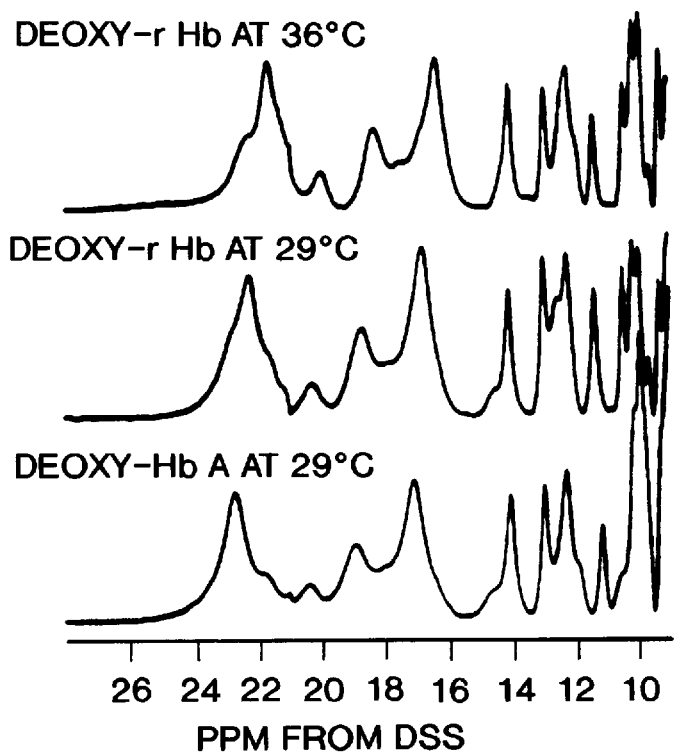

The $^1$H-NMR spectra of FIGS. 4A and 4B were obtained for 4% Mono S-purified r Hb (α96Val→Trp) from pHE202/JM109 from peak a and 4% Hb A, both in their deoxy forms, as described above, in 0.1M phosphate in $H_2O$ at pH 7.0. The FIG. 4A spectra were obtained at 29° C.; those of FIG. 4B were obtained at 29° C. and 36° C. as indicated in the figure. Hyperfine-shifted $N_δH$ exchangeable proton resonances of the proximal histidine residues are shown in FIG. 4A. For FIG. 4A the resonance at ~63 ppm was assigned to the hyperfine-shifted $N_δH$-exchangeable proton of the proximal histidine residue (α87His) of the β chain of deoxy-Hb A, and the resonance at ~77 ppm was assigned to the corresponding residue of the β chain (β92His) of deoxy-Hb A (Takahashi, S., et al., *Biochemistry* 19:5196 (1980), and La Mar, G. N., et al., *Biochem. Biophys. Res. Commun.* 96:1172 (1980), the disclosures of which are incorporated herein by reference.) The chemical shift positions of these two proximal histidyl resonances in peak a of r Hb (α96Val→Trp) are the same as those of Hb A as seen in FIG. 4A. This indicates that there are no pertubations around the proximal histidines of r Hb (α96Val→Trp).

The ferrous hyperfine-shifted and exchangeable proton resonances of r Hb (α96Val→Trp) of peak a and Hb A in their deoxy form are shown in FIG. 4B. The hyperfine-shifted resonances arise from the protons on the heme groups and their nearby amino acid residues due to the hyperfine interactions between protons and unpaired electrons of Fe(II) in the heme iron atoms. The hyperfine-shifted resonances of r Hb (α96Val→Trp) from peak a at 29° C. show some chemical shift changes around the resonances at ~22.5 and ~18.7 ppm from DSS (assigned to the protons associated with the β chains of deoxy-Hb A) (Takahashi, et al., 1980) and at ~17 ppm from DSS (assigned to the protons associated with the α chains of deoxy-Hb A) (Takahashi, et al., 1980) compared to those of Hb A at 29° C. The exchangeable $^1$H resonances over the spectral region from 11 to 14 ppm from DSS are known to be excellent markers for the deoxy-quaternary structure of Hb A (Ho, C., *Advanc. Protein Chem.* 43:153 (1992)). The resonance at ~14 ppm has been assigned to the intersubunit hydrogen bond between α42Tyr and β99Asp, a characteristic feature of the deoxy-quaternary (T) structure (Fung, L. W.-M., et al., *Biochemistry* 14:2526 (1975), the disclosure of which is incorporated herein by reference). As seen in FIG. 4B, there is no noticeable difference in the resonance at ~14 ppm from DSS between Hb A and r Hb (α96Val→Trp) from peak a in the deoxy form, which indicates that this $α_1β_2$ intersubunit hydrogen bond of the deoxy form is unperturbed by the mutation.

In r Hb (α96Val→Trp), a new resonance appeared at ~12.6 ppm from DSS at 29° C. as seen in FIG. 4B, which is absent in deoxy-Hb A. However, when the $^1$H-NMR spectrum was taken at high temperature (36° C.), the resonance at ~12.6 ppm from DSS shifted. The temperature-sensitive chemical shift position indicates that this new resonance is likely to be hyperfine-shifted resonance rather than an exchangeable resonance (Jesson, J. P., *J. Chem. Phys.* 47:579 (1967); Kurland, R. J., et al., *J. Magn. Reson.* 2:286 (1970); Johnson, M. E., et al., *J. Am. Chem. Soc.* 99:1245 (1977), the disclosures of which are incorporated herein be reference).

The foregoing results indicate that MD simulations can be applied successfully for the transformation from the wild-type (HbA) to mutant Hb ((96Val→Trp).

iii. Switching of Quaternary Structure without Changing the Ligation State

Figure 5A:
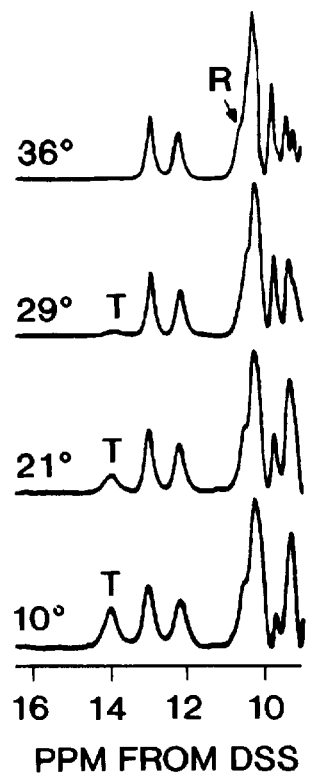
FIGS. 5A–5D are $^1$H-NMR spectra showing the effects of temperature on the 300-MHz proton resonances of 4% r HbCO (α96Val→Trp) from peak a derived from pHE202/JM109 and 4% HbCO A in the presence of 10 mM inositol hexaphosphate ("IHP") in 0.1M phosphate at pH 7.0 and at 10, 21, 29 and 36° C.
Figure 5B:
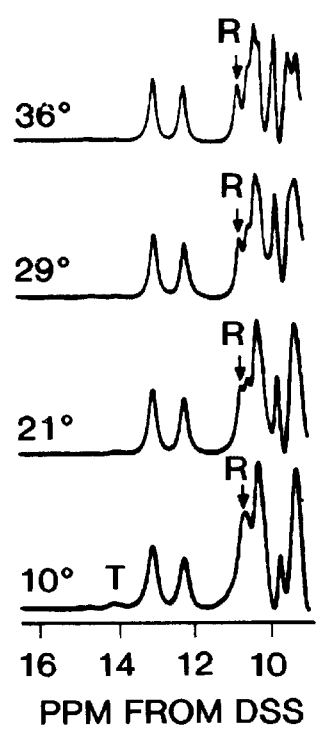
Figure 5C:
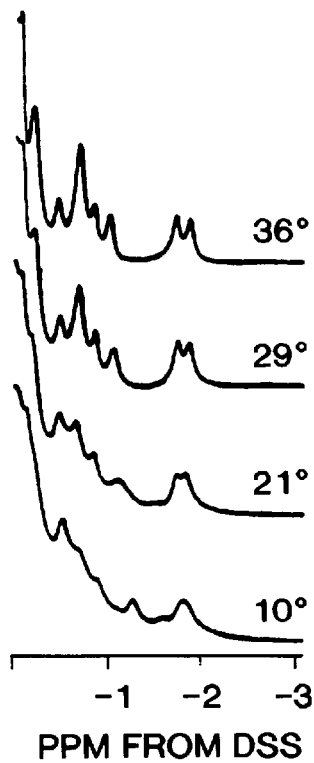
Figure 5D:
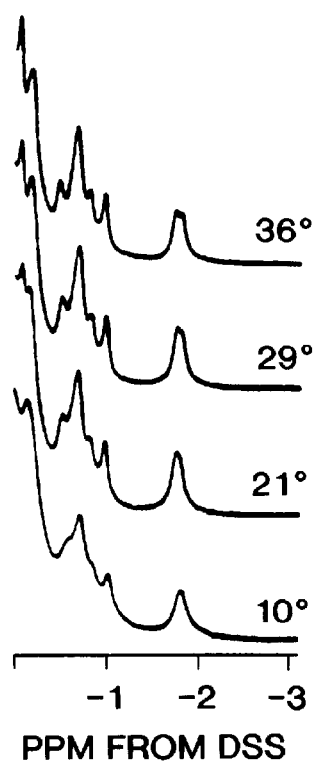

The exchangeable proton resonances of r Hb ($\alpha$96Val→Trp) in the CO form in the presence of 10 mM inositol hexaphosphate ("IHP") (Sigma) exhibit some very interesting and unique features compared to those of Hb A. $^1$H-NMR spectra were obtained of 4% r HbCO ($\alpha$96Val→Trp) derived from pHE202/JM109 peak a and 4% HbCO A at 300 MHz in the presence of 10 mM IHP in 0.1M phosphate in $H_2O$ at pH 7.0. Spectra were obtained at 10°, 21°, 29°, and 36° C. FIGS. 5A and 5B show exchangeable proton resonances of r HbCO ($\alpha$96Val→Trp) and HbCO A, respectively. FIGS. 5C and 5D show ring-current shifted resonances of r HbCO ($\alpha$96Val→Trp) and HbCO A, respectively.

The resonance at ~10.7 ppm from DSS, a characteristic feature of the oxy-quaternary (R) structure (the intersubunit hydrogen bond between $\alpha$94Asp and $\beta$102Asn) (Fung, L. W.-M., et al., *Biochemistry* 14:2526 (1975); Shaanan, B., *J. Mol. Biol.* 171:31 (1983), the disclosure of which is incorporated herein by reference), disappears in the presence of IHP in the $^1$H-spectrum of r HbCO ($\alpha$96Val→Trp) at 29° C. (FIG. 5A). Instead, FIG. 5A shows the resonance at ~14 ppm from DSS, a characteristic feature of the deoxy-quaternary (T) structure (the intersubunit hydrogen bond between $\alpha$42Tyr and $\beta$99Asp) (Fung, et al., 1975; Fermi, G., et al., *J. Mol. Biol.* 175:159 (1984), the disclosure of which is incorporated herein by reference) appears as compared to HbCO A (FIG. 5B).

As will be shown below, with reference to FIG. 5, the presence of a strong allosteric effector, IHP, appears to stabilize the deoxy form of r Hb ($\alpha$96Val→Trp), and thus can shift the equilibrium toward the deoxy form. The presence of new hydrogen bonds in the $\alpha_1\beta_2$ and $\alpha_2\beta_1$ subunit interfaces can add extra stability and make the quaternary structural transition toward the deoxy-quaternary structure much easier in the presence of IHP, especially at lower temperatures.

In FIG. 5A, the intensity of the resonance at ~14 ppm from DSS gradually increases in the spectrum of r Hb ($\alpha$96Val→Trp) as the temperature is decreased from 29 to 10° C. At 36° C., the resonance at ~14 ppm from DSS disappears, and the resonance at ~10.7 ppm from DSS, a characteristic feature of the oxy-quaternary (R) structure, reappears as a shoulder. The relative intensity of the resonance at ~14 ppm at 10° C. is similar to that of the exchangeable resonance in the deoxy form of r Hb ($\alpha$96Val→Trp). The chemical shift position of this resonance at ~14 ppm from DSS does not change with temperature, suggesting that the origin of this resonance is exchangeable rather than hyperfine shifted. The appearance of the resonance at ~14 ppm from DSS is not accompanied by the appearance of the hyperfine-shifted resonances from ~11 to ~24 ppm, indicating that the heme iron is still in the low-spin, diamagnetic state (i.e., ligand-bound form). The change of intensity with temperature of the resonances which are characteristics of the deoxy- (T-) and oxy- (R-) quaternary structures is reversible.

FIG. 5B shows that there is very little variation of the exchangeable proton resonances of HbCO A in 10 mM IHP as a function of temperature, contrary to that observed for r HbCO ($\alpha$96Val→Trp) in FIG. 5A. Even at 1° C., it appears that there is only a very small signal at ~14 ppm for HbCO A, very different in intensity compared to that for r HbCO ($\alpha$96Val→Trp). At intermediate temperatures, such as 21° and 29° C., the exchangeable proton resonances of r HbCO ($\alpha$96Val→Trp) in the presence of IHP show that the resonance at ~10.7 ppm, a characteristic feature of the oxy-quaternary structure, essentially disappears, but the resonance at ~14 ppm, a characteristic feature of the deoxy-quaternary structure, exhibits only very weak intensity. These results suggest that an intermediate quaternary structure may exist which loses a hydrogen bond between $\alpha$94Asp and $\beta$102Asn, manifested by the resonance at ~10.7 ppm, but which still does not form a hydrogen bond between $\alpha$42Asp and $\beta$99Asp, manifested by the resonance at ~14 ppm. This r HbCO ($\alpha$96Val→Trp) of the present invention can be gradually converted to the deoxy-like quaternary structure without changing the ligation state by just the addition of a strong allosteric effector, IHP, and/or by lowering the temperature.

The ring-current shifted proton resonances of r Hb ($\alpha$96Val→Trp) and Hb A in the CO form in the presence of 10 mM IHP were also compared at different temperatures as shown in FIGS. 5C and 5D. The relative intensity and the chemical shift position of the resonances over the region from 0 to −1.1 ppm from DSS of r HbCO ($\alpha$96Val→Trp) were seen to vary a great deal with temperature, while those of Hb A vary relatively little. The resonances from −1.7 to −1.8 ppm from DSS, assigned to the $\gamma_2$-methyl groups of the E11Val (distal valine) of the $\alpha$ and $\beta$ chains of HbCO A (Lindstrom, T. R., et al., *Biochemistry* 11:1677 (1972); Dalvit, C., et al., *Biochemistry* 24:3398 (1985), the disclosures of which are incorporated herein by reference), merge into one peak at low temperature in the CO form of both r Hb ($\alpha$96Val→Trp) and Hb A. The resonances from −11.7 to −1.8 ppm from DSS or r Hb ($\alpha$96Val→Trp) are seen to be much broader than those of Hb A. It is believed that change in the relative intensity and the chemical shift position of the resonances over the region from 0 to −1.1 ppm from DSS and the broadening of the resonances from −1.7 to −1.8 ppm of r Hb ($\alpha$96Val→Trp) may reflect structural transitions which are not observed in Hb A.

Figure 6A:
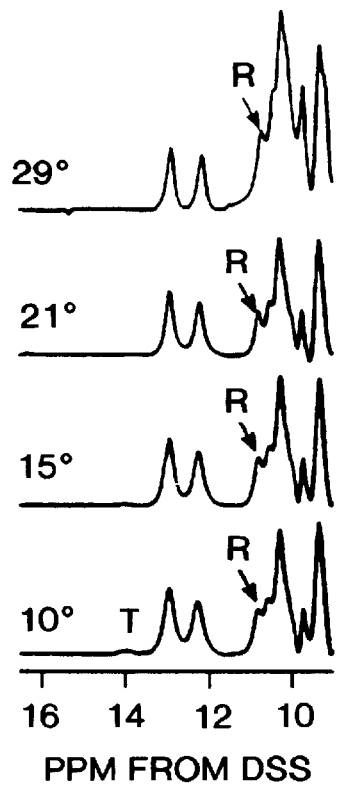
FIGS. 6A–6D are $^1$H-NMR spectra showing the effects of temperature on the 300-MHz proton resonances of 4% r HbCO (α96Val→Trp) from peak a derived from pHE202/JM109 and 4% HbCO A in the absence of IHP in $H_2O$ at pH 7.0, and at 10, 15, 21, and 29° C.
Figure 6B:
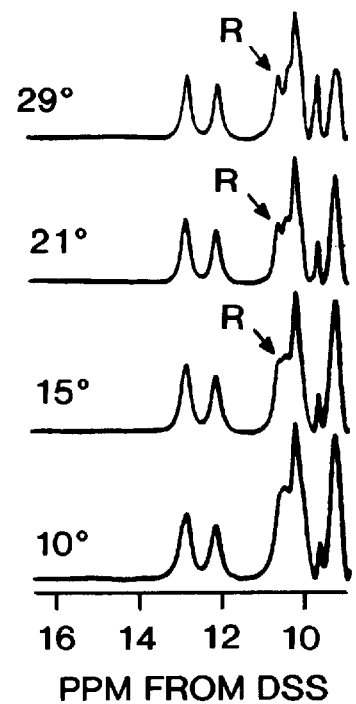
Figure 6C:
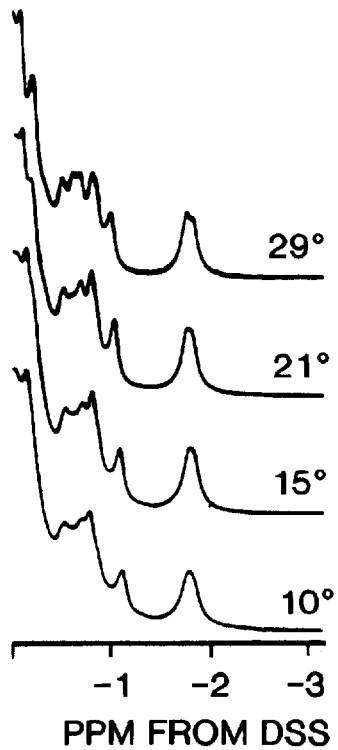
Figure 6D:
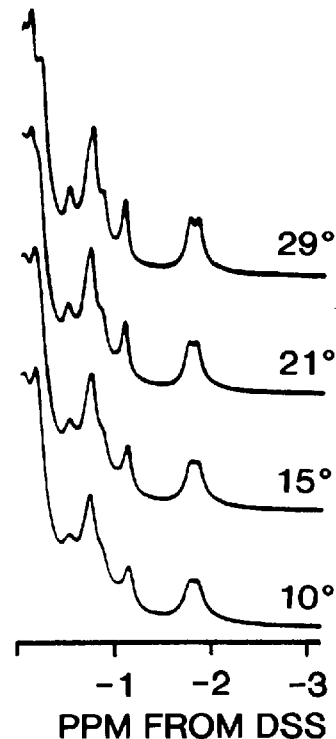

$^1$H-NMR spectra were also obtained of 4% r HbCO ($\alpha$96Val→Trp) from peak a and 4% HbCO A at 300 MHz, without any IHP present, in 0.1M phosphate in $H_2O$ at pH 7.0. Spectra obtained at the exchangeable proton resonances of r Hb ($\alpha$96Val→Trp) and Hb A in the CO form in the absence of IHP at different temperatures are compared in FIGS. 6A and 6B. As the temperature is decreased, the resonance at ~14 ppm from DSS appears in r Hb ($\alpha$96Val→Trp) in the absence of IHP, while Hb A shows no appearance of the resonance at ~14 ppm from DSS, even at 10° C. FIGS. 6C and 6D show the ring-current shifted resonances of r Hb ($\alpha$96Val→Trp) and HbCO A in the CO form, respectively, in the absence of IHP. These figures also show spectral changes depending on the temperature.

The relative intensity and the chemical shift position of the resonances over the region from 0 to −1.1 ppm from DSS of r HbCO ($\alpha$96Val→Trp) were seen to vary greatly with temperature, while those of HbCO A were seen to vary little. The appearance of the exchangeable resonance at ~14 ppm from DSS, a characteristic feature of the deoxy-quaternary structure, at a low temperature (FIGS. 6A and 6B), and the changes in the relative intensity and the chemical shift position of the resonances over the ring-current shifted region from 0 to -1.1 ppm from DSS of r HbCO (α96Val→Trp) (FIGS. 6C and 6D) suggest that a deoxy-quaternary structural conversion occurs even in the absence of IHP.

Oxygen-Binding Properties of r Hb (α96Val→Trp)

0.1 mM of each of the Hbs of the three peaks of r HbCO$_2$ (α96Val→Trp) derived from pHE202/JM109 (peaks a, b$_1$, and b$_2$) in 0.1M phosphate at pH 7.0 were applied to a column of Sephadex G-75. Each eluted as a symmetrical peak in the position corresponding to that of HbO$_2$ A, indicating that all three forms of r Hb (α96Val→Trp) in the oxy form are tetrameric under the present experimental conditions (results not shown).

Figure 7A:
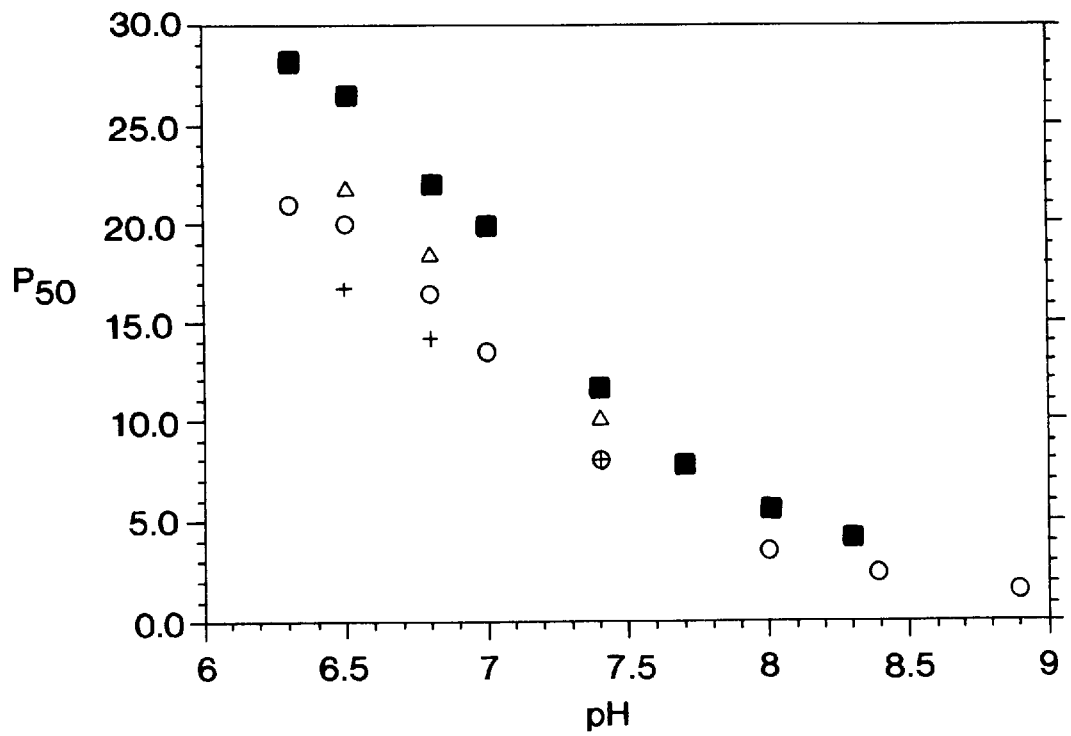
FIGS. 7A and 7B show oxygen affinity with partial $O_2$ pressure at 50% saturation ($P_{50}$) (mmHg) plotted as a function of pH obtained with a 0.1 mM of Hb A or r Hb (α96Val→Trp) derived from pHE202/JM109 in 0.1M sodium phosphate buffer in the pH range 6.3–8.9 at 29° C.
Figure 7B:
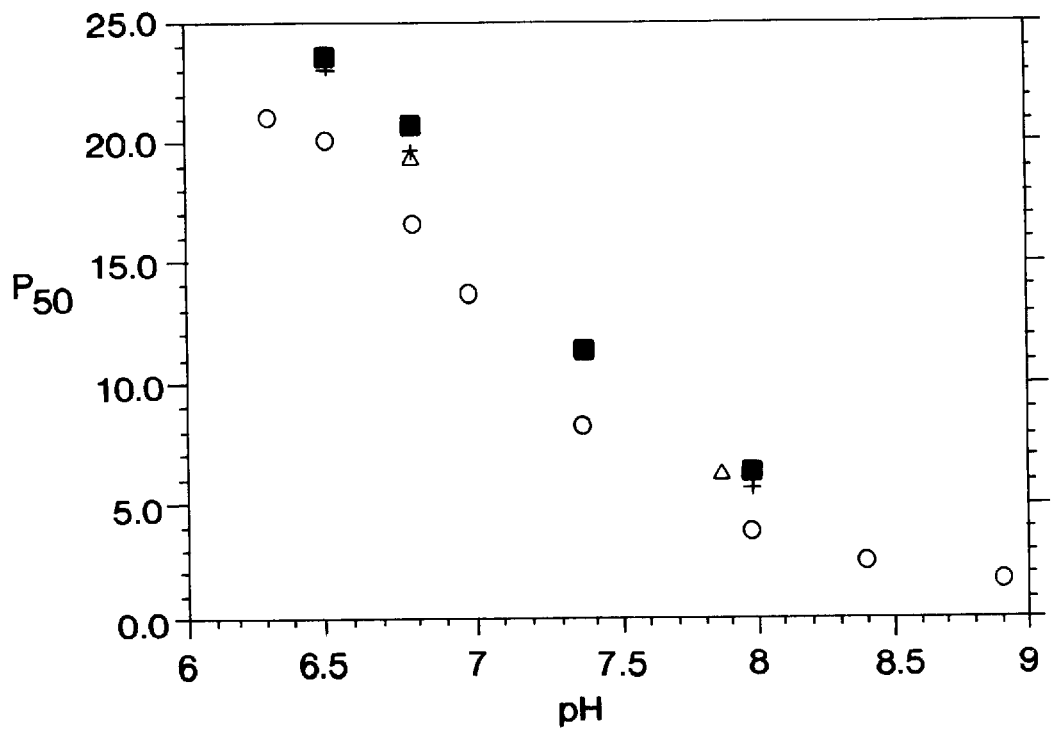

The oxygen-binding properties of peaks a, b$_1$, and b$_2$ of r Hb (α96Val→Trp) as a function of pH were investigated as described above. Briefly, oxygen dissociation data were obtained with 0.1 mM concentration of each particular Hb used in 0.1M sodium phosphate buffer in the pH range 6.3–8.9 at 29° C. Partial O$_2$ pressure at 50% saturation P$_{50}$) was determined from each curve. The data for FIG. 7A were obtained from pHE202/JM109-derived Mono S-purified fractions, peaks a, b$_1$, and b$_2$ from pHE202/JM109 and Hb A. The data for FIG. 7B were obtained from pHE202/JM109-derived Mono S-purified fractions, peaks a, b$_1$, and b$_2$ and Hb A that were converted from their respective CO forms to their Fe$^{+3}$ forms, and then back to their CO forms as described above. For both FIGS. 7A and 7B, Hb A is (○); r Hb (α96Val→Trp) from peak a is (■); r Hb (α96Val→Trp) from peak b$_1$ is (Δ); and r Hb (α96Val→Trp) from peak b$_2$ is (+). As seen in FIGS. 7A and 7B, r Hbs (α96Val→Trp) from peaks b$_1$, and b$_2$ shows similar P$_{50}$ (partial O$_2$ pressure at 50% saturation) values to that of Hb A before the oxidation and reduction process, whereas, r Hb (α96Val→Trp) from peak a and "converted" Hbs from peaks b$_1$, and b$_2$ exhibit a significantly lower oxygen affinity.

Figure 8A:
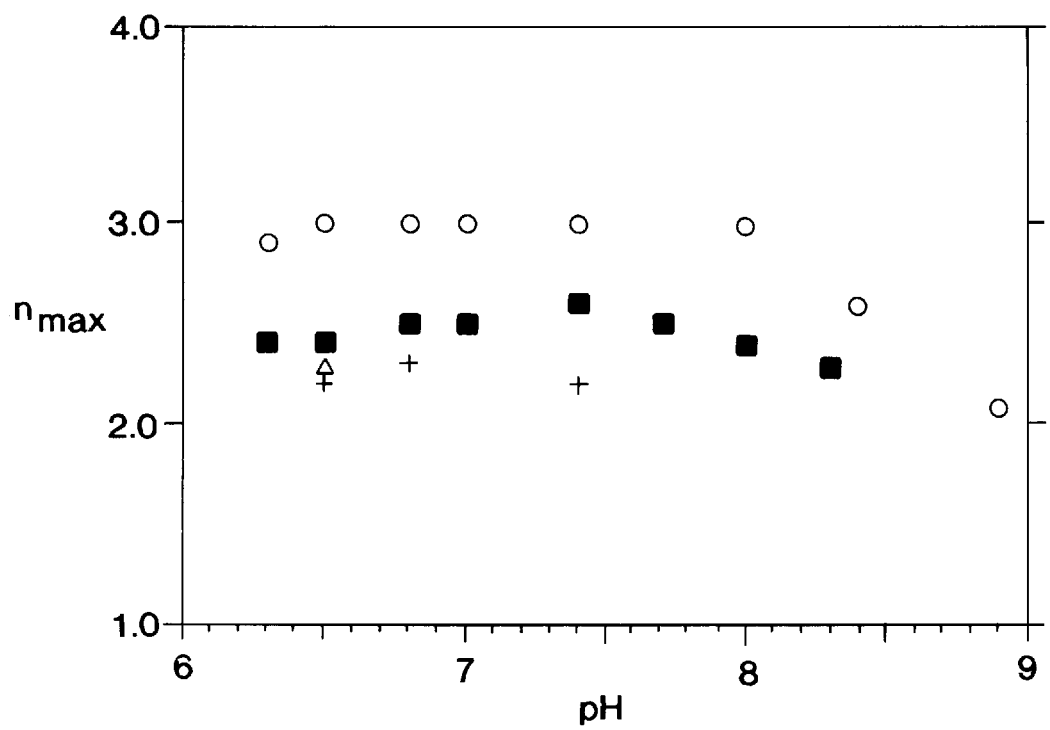
FIGS. 8A and 8B show the Hill coefficient ($n_{max}$) as a function of pH in which oxygen dissociation data were obtained with 0.1 mM concentration of Hb A or r Hb (α96Val→Trp) derived from pHE202/JM109 in 0.1M sodium phosphate buffer in the pH range 6.5–8.4 at 29° C.
Figure 8B:
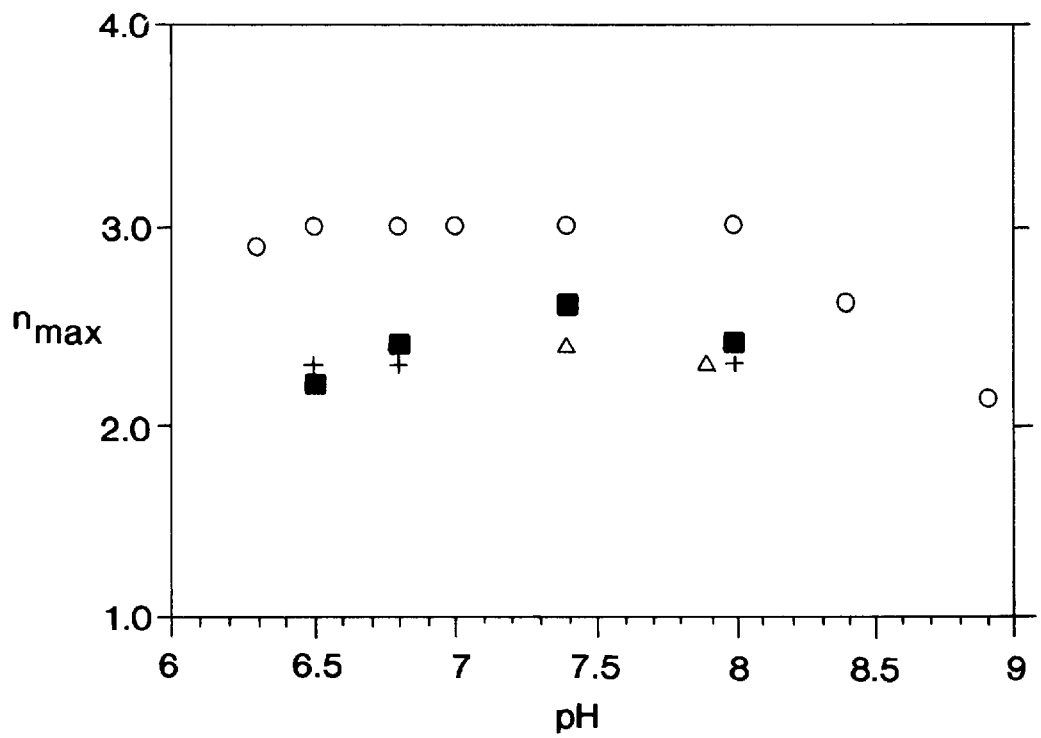

The Hill coefficient (n$_{max}$) was determined for Mono S-purified peaks a, b$_1$, and b$_2$ of r Hb (α96Val→Trp) derived from pHE202/JM109 and Hb A both for their respective unmodified forms as well as for their forms which were converted from their CO respective forms to their Fe$^{+3}$ states and then back to their CO forms. Oxygen dissociation data were obtained as described above. Briefly, the data for each Hb sample was obtained with 0.1 mM concentration of Hb in 0.1M sodium phosphate in the pH range 6.5–8.4 at 29° C. The Hill coefficient was determined from each curve. FIG. 8A shows data obtained from the various unmodified hemoglobins; FIG. 8B shows data obtained from the hemoglobins that were converted from CO forms to Fe$^{+3}$ states and back to CO forms. In both figures, Hb A is (○); r Hb (α96Val→Trp) from peak a is (■); r Hb (α96Val→Trp) from peak b$_1$ is (Δ); and r Hb (α96Val→Trp) from peak b$_2$ is (+).

FIGS. 8A and 8B show that r Hb (α96Val→Trp) from peak a and "converted" Hbs exhibit about 90% of the Bohr effect (ΔlogP$_{50}$/ΔpH) of Hb A and exhibit cooperativity with n$_{max}$ values of about 2.2 to 2.6 depending on the pH, compared to about 3 for Hb A.

Table 1 below compares the values of P$_{50}$ and n$_{max}$ for r Hb (α96Val→Trp) from peak a derived from pHE202/JM109, r Hb A (prepared in our laboratory according to Shen, T.-J., et al., *Proc. Natl. Acad. Sci. USA* 90:8108 (1993)), Hb A, and Hb A in the presence of 5 mM of 2,3-DPG. r Hb (α96Val→Trp) from peak a shows similar oxygen-binding properties to those of Hb A in the presence of 2,3-DPG. Thus, it is believed that due to the unique structure of r Hb (α96Val→Trp), even in the absence of an allosteric effector, it has properties similar to those of Hb A in the presence of an allosteric effector.

TABLE 1

| | r Hb(α96Val→Trp) from peak a | | r Hb A | | Hb A | | Hb A + 2, 3-DPG | |
|---|---|---|---|---|---|---|---|---|
| pH | P$_{50}$ (mm Hg) | n$_{max}$ | P$_{50}$ (mm Hg) | n$_{max}$ | P$_{50}$ (mm Hg) | n$_{max}$ | P$_{50}$ (mm Hg) | n$_{max}$* |
| 6.5 | 26.6 | 2.4 | 19.8 | 3.0 | 20.0 | 3.0 | 26.3 | 2.7 |
| 6.8 | 22.0 | 2.5 | 17.3 | 2.9 | 16.5 | 3.0 | 23.4 | 2.8 |
| 7.4 | 11.6 | 2.6 | 7.3 | 2.9 | 8.0 | 3.0 | 11.1 | 2.9 |
| 8.0 | 5.6 | 2.4 | 3.6 | 2.9 | 3.5 | 3.0 | 3.8 | 2.7 |

*Experimental Error ±10%

Figure 9:
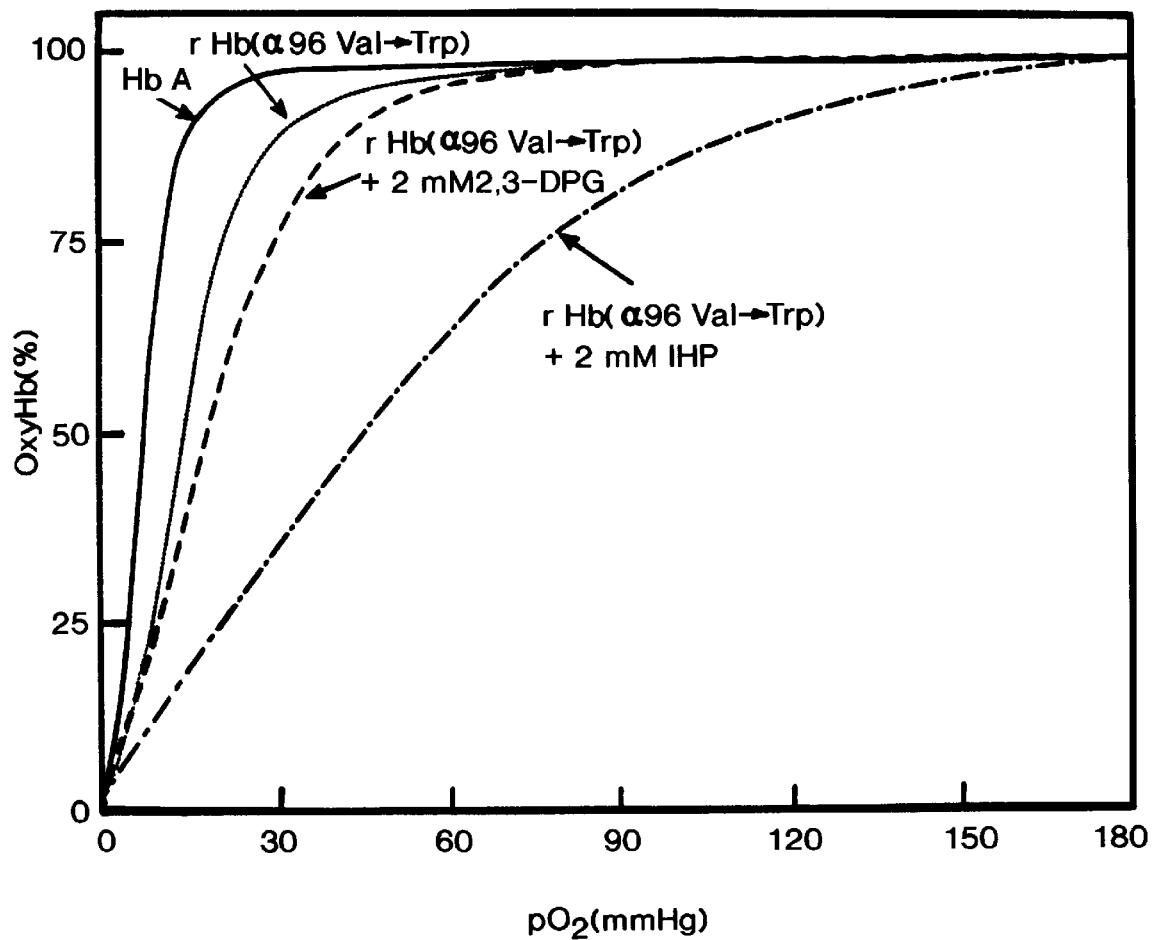
FIG. 9 shows oxygen dissociation curves obtained with 0.1 mM Hb in 0.1M sodium phosphate buffer at pH 7.4 and 29° C. of Mono S-purified r Hb (α96Val→Trp) from peak a derived from pHE202/JM109 and Hb A as compared to Mono S-purified r Hb (a96Val→Trp) from peak a in the presence of allosteric effectors: 2 mM 2,3-DPG and 2 mM IHP.

Oxygen-dissociation data were also obtained with 0.1 mM of each of the following hemoglobin samples in 0.1M sodium phosphate buffer at pH 7.4 and 29° C. Curves were determined for Hb A, r Hb (α96Val→Trp) (pHE202/JM109), r Hb (α96Val→Trp) in the presence of 2 mM 2,3-DPG, and r Hb (α96Val→Trp) in the presence of 2 mM IHP. The results are shown in FIG. 9. In addition to low oxygen affinity and high cooperativity, the oxygen-binding curve of r Hb (α96Val→Trp) from peak a shows a unique oxygen binding property. At very low oxygen pressure, oxygen binding of r Hb (α96Val→Trp) from peak a in the presence of an allosteric effector, such as 2,3-DPG or IHP, shows a biphasic curve.

Figure 10A:
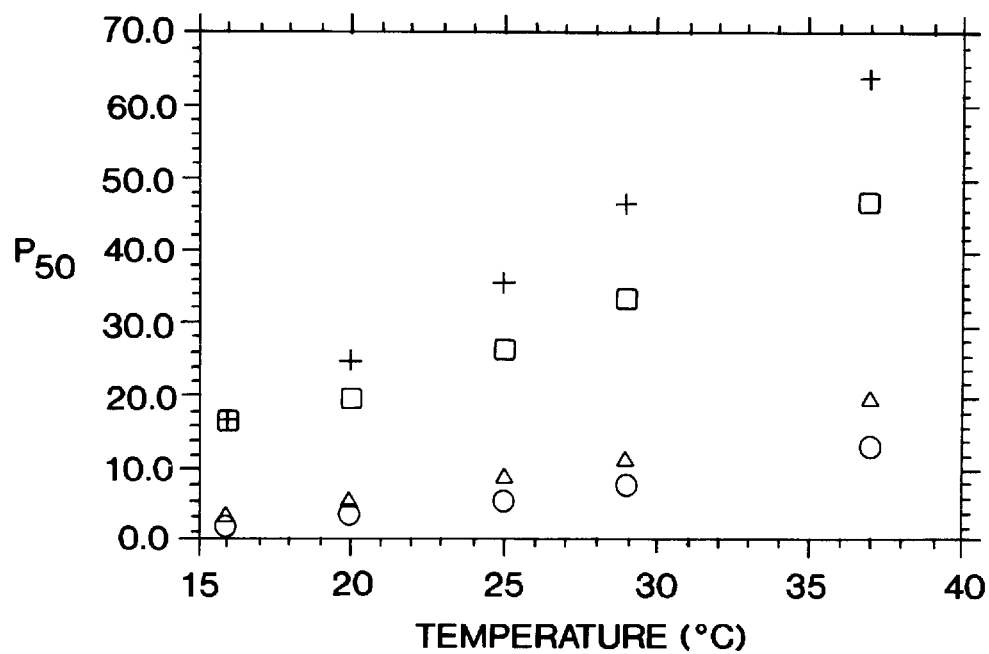
FIGS. 10A and 10B show respectively, the temperature dependence of oxygen affinity $P_{50}$) and the Hill coefficient ($n_{max}$) obtained with 0.1 mM Hb A or r Hb (α96Val→Trp) derived from pHE202/JM109 in 0.1M sodium phosphate buffer at pH 7.4, and at 16, 20, 25, 29, and 37° C. The Hbs used were: Hb A (○), r Hb (α96Val→Trp) (Δ), r Hb (α96Val→Trp) in the presence of 2 mM IHP (+) and Hb A in the presence of 2 mM IHP (■).
Figure 10B:
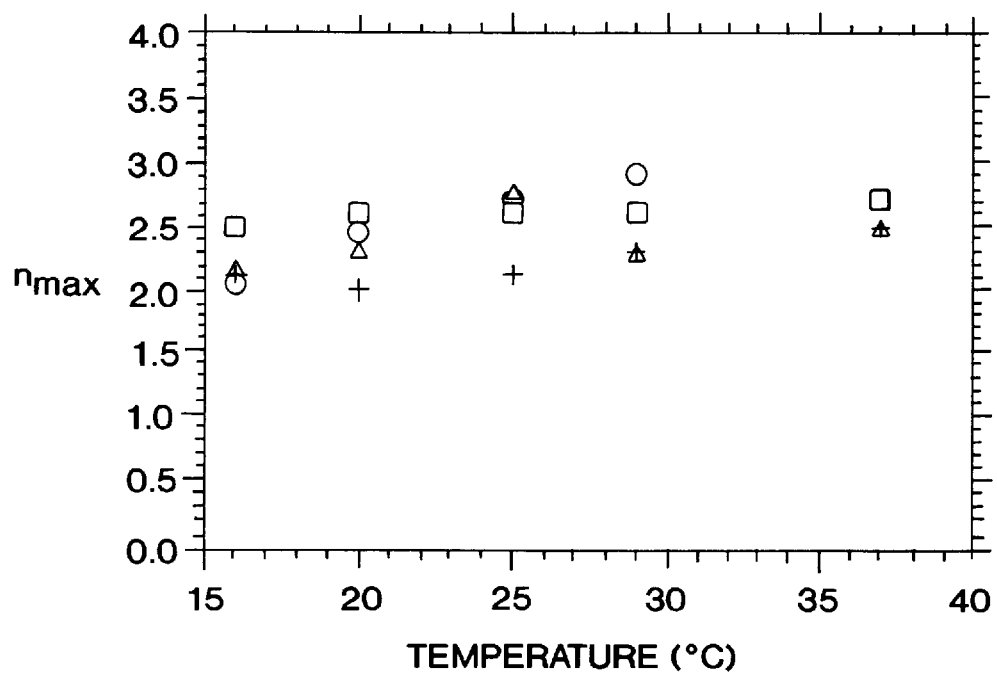

The effect of temperature on the oxygen affinity P$_{50}$) and Hill coefficient (n$_{max}$) of r Hb (α96Val→Trp) from peak a and Hb A are compared in FIGS. 10A and 10B, respectively.

The oxygen dissociation data for the various Hb samples were obtained as described above with 0.1 mM concentration of each Hb sample in 0.1M sodium phosphate buffer at pH 7.4. The temperatures were 16°, 20°, 25°, 29°, and 37° C. The P$_{50}$ and Hill coefficient (n$_{max}$) were determined from each curve. Data was obtained for Hb A (○); r Hb (α96Val→Trp) (pHE202/JM109) from peak a (Δ); r Hb (α96Val→Trp) (pHE202/JM109) in the presence of 2 mM IHP (+) and Hb A in the presence of 2 mM IHP (□). FIG. 10A shows oxygen affinities P$_{50}$); FIG. 10B shows Hill coefficients (n$_{max}$)

As shown in FIG. 10A, the oxygen affinity is increased significantly in r Hb (α96Val→Trp) and Hb A, both in the presence of IHP and in the absence of IHP, as the temperature is decreased. However, FIG. 10B shows that the n$_{max}$ values of r Hb (α96Val→Trp) and Hb A do not change much as a function of temperature. Over the temperature range from 15° to 37° C., both r Hb (α96Val→Trp) and Hb A exhibit cooperativity with n$_{max}$ values of about 2.0 to 2.9.

B. Plasmid DHE702

Construction of Expression Plasmid PHE702

A similar α96Val→Trp mutation was introduced into plasmid pHE7 with oligonucleotide 5'-AGCTTGAAGTTCCAT-GGGTCCACCC-3' (SEQ. ID NO: 26 DNA International, Inc., Lake Oswego, Oreg.) to form plasmid pHE702 according to published methods (Kunkel, T. M. 1985, Proc. Natl. Acad. Sci. USA 82:488–492; Shen, T.-J., et al., 1993 Proc. Natl. Acad. Sci. USA 90:8108).

The plasmid pHE7 is a plasmid coexpressing human α- and β-cDNAs and the E. coli Met-AP gene. It contains the two expression cassettes arranged in tandem in the same orientation as for pHE2 described above: (i) tac promoter—E. coli Met-AP coding sequence—5ST1T2 terminator and (ii) tac promoter—α-globin cDNA coding sequence—β-globin cDNA coding sequence—5ST1T2 terminator.

The plasmid pHE702 was constructed in a manner similar to that used to construct pHE2 as set forth above, except: (1) the synthetic human α-globin gene was replaced by the human α-globin cDNA; (2) the synthetic human β-globin gene was replaced by the human β-globin cDNA; and (3) the E. coli Met-AP coding sequence was directly obtained from E. coli genomic DNA rather than from plasmid pSYC1174.

The human α-globin cDNA coding sequence was obtained by PCR with pKT218-αc (a gift, kindly provided by B. G. Forget, Yale University and available on request) as the template and two synthesized primers 5'-GAGAACCCCATAT-GGTGCTGTCTCCTGCC-3' SEQ ID NO: 7 and 5'-CCGAGGCACTAGTTTAACGGTATTTG-GAGGTC-3' (SEQ. ID NO: 8 both from DNA International, Inc.), which are complementary to the 5'- and 3'- end sequences of the human α-globin cDNA and respectively contain a NdeI site and a SpeI site.

The human β-globin cDNA coding sequence was obtained by PCR with pβ which was constructed according to the protocol of Groebe, et al., *Protein Expression and Purification* 3:134 (1992) as template and two synthesized primers 5'-CAAACAGACCATATGGTGCACCTGACTC-CTGAGGAG-3, SEQ. ID NO: 9 and 5'-AGCAAGAATG-CATGCTTAGTGATACTTGTGGGCCAGG-3, (SEQ. ID NO: 10 both from DNA International, Inc.), which are complementary to the 5'- and 3'- end sequences of the human β-globin cDNA and respectively contain a NdeI site and a NsiI site.

The coding sequence of E. coli Met-AP gene was obtained by PCR with E. coli genomic DNA as template and two synthesized primers, 5'-TGGACAGAATTCCATGGCTATCTC-AATCA-3' SEQ. ID NO: 11 and 5'-TGGCTTAAGCTTATTCGTCGTGCGAG-3, (SEQ. ID NO: 12 both from DNA Synthesizing Facility, University of Pittsburgh), which are complementary to the 5'- and 3'- end sequences of the E. coli Met-AP gene and respectively contain an EcoRI site and a HindIII site. Plasmid pHE702 in host cell E. coli JM109 and designated pHE702/JM109 was deposited with the American Type Culture Collection of Rockville, Md., on Apr. 26, 1995 under number ATCC 69793.

Comparison of r Hb (α96Val→Trp) from plasmids pHE202 and pHE702

The growth conditions for E. coli JM109 harboring pHE702 are identical to those set forth above for pHE202. The yield of r Hb (α96Val→Trp) derived from pHE702 is about 50% that of r Hb (α96Val→Trp) derived from pHE202 set forth above. As noted above, pHE702 was constructed from human genes and thus other expression systems may be advantageously used. The elution profile for r Hb (α96Val→Trp) derived from pHE702 gives two peaks after Mono S chromatography, labeled peak 1 and peak 2 (results not shown). Similarly, all other analytical procedures as described above for r Hb (α96Val→Trp) derived from pHE202 were performed the same way for the pHE702-derived hemoglobin.

A comparison of both the functional and structural properties of the low oxygen affinity r Hb (α96Val→Trp) derived from the two different plasmids, pHE202 and pHE702 was carried out. A detailed description of r Hb (α96Val→Trp) derived from pHE202 is described above. r Hb (α96Val→Trp) derived from pHE202 and pHE702 were oxidized and reduced as described above and their $P_{50}$ and $n_{max}$ values were measured in 0.1M sodium phosphate at 29° C. at pH 6.8 and 7.4 and compared to those for Hb A. Table 2 below summarizes the oxygen-binding properties of Hb A, r Hb (α96Val→Trp) derived from pHE202, and r Hb (α96Val→Trp) derived from pHE702 at pH 6.8 and 7.4. It is clear that the functional properties as exhibited by r Hb (α96Val→Trp) derived from both plasmids are essentially identical.

TABLE 2

| | $P_{50}$ (mm Hg)* pH | | $n_{max}$* pH | |
|---|---|---|---|---|
| | 6.8 | 7.4 | 6.8 | 7.4 |
| Hb A | 17.2 | 8.0 | 3.1 | 3.0 |
| r Hb (α96Val→Trp) derived from pHE202 (peak b₂) | 20.6 | 11.2 | 2.4 | 2.6 |
| r Hb (α96Val→Trp) derived from pHE702 (peak 2) | 22.8 | 11.7 | 2.4 | 2.8 |

*Experimental error of ±10%

FIG. 11 shows the ¹H-NMR spectra of Hb A and r Hb (α96Val→Trp) derived from pHE202 and pHE702 in the CO form in 0.1M phosphate at pH 7.0 and 29° C., carried out as described in detail above. FIG. 11A shows the exchangeable proton resonances and FIG. 11B shows the ring-curent shifted proton resonances of Hb A and r Hb (α96Val→Trp) derived from pHE202 (peak b₂) and pHE702 (peak 2) in the CO form. Both sets of ¹H-NMR results indicate that there is no observable difference in the ¹H-NMR spectra between these two r Hb (α96Val→Trp). Thus, it is concluded that there is no observable structural or functional differences between r Hb (α96Val→Trp) derived from pHE202 and pHE702.

C. MD Simulations

The distance between the Cα of the two α96Val residues in the crystal structure of deoxy Hb A is 10.3 angstroms (Fermi, G., et al., *J. Mol. Biol.* 175:159 (1984), the disclosure of which is incorporated herein by reference). The size of the tryptophan residue located in the α96 position of r Hb (α96Val→Trp) would lead one to expect that the stability of r Hb (α96Val→Trp) would be highly dependent on the side-chain angle orientation of the tryptophan residue. Initial computer modeling of the deoxy form indicates that out of the four side-chain angles of tryptophan which show more than 10% incidence from the rotamer library (Ponder, J. W., et al., *J. Mol. Biol.* 193:775 (1987), the disclosure of which is incorporated herein by reference), only the tryptophan with the side-chain angles $\chi_1$=64.8 and $\chi_2$=−88.9 (20.7%) gives a stable conformation. The other three tryptophan conformations all direct toward each other, giving unfavorable non-bonding interactions.

The transformation between wild-type and mutant Hbs was carried out with all four possible side-chain angles of the tryptophan residue. The distance between the $N\epsilon_1$ Trp96 residues in the two α-chains and the side-chain angles of each α96Trp residue in the average simulated structure in the deoxy form are summarized in Table 3 below.

TABLE 3

| Rotamer Library* | | $\alpha_1$Trp96 | | $\alpha_2$Trp96 | | Distance |
|---|---|---|---|---|---|---|
| $\chi_1$ (deg) | $\chi_2$ (deg) | $\chi_1$ (deg) | $\chi_2$ (deg) | $\chi_1$ (deg) | $\chi_2$ (deg) | $N\epsilon_1(\alpha_1)$–$N\epsilon_1(\alpha_2)$ (angstroms) |
| −70.4 ± 7.0 (37.9%) | 100.5 ± 18.2 | −63.3 | −176.3 | −88.5 | 128.9 | 7.7 |
| 64.8 ± 13.0 (20.7%) | −88.9 ± 5.3 | 92.3 | −71.0 | 96.2 | −78.7 | 17.3 |
| −177.3 ± 7.9 (13.8%) | −95.1 ± 7.6 | −86.5 | 89.9 | −174.2 | −116.3 | 10.2 |
| −179.5 ± 3.4 (10.3%) | 87.5 ± 3.8 | −118.0 | 89.5 | −177.1 | 71.8 | 5.6 |

*From Ponder, J. W., et al., J. Mol. Biol. 193:775 (1987)

Only the simulated structure from the initial tryptophan side-chain angles of $\chi_1=64.8$ and $\chi_2=-88.9$ shows both α96Trp with a relatively symmetrical conformation. The side-chain angles of both α96Trp residues in this conformation are relatively well preserved, and the distance between the $N\epsilon_1$ of the two α96Trp residues indicates that the α96Trp residues are sufficiently separated so as not to affect each other. These results suggest that the tryptophan side-chain angles of $\chi_1=64.8$ and $\chi_2=-88.9$ may be the closest to the natural conformation.

Thus, in order to make the analysis of the free energy of simulation easier, for the calculation of the free energy of cooperativity, MD simulations were carried out with side-chain angles of $\chi_1=64.8$ and $\chi_2=-88.9$ on a sphere centered on the center of mass coordinate of $C_\beta$ of β99Asp of the crystal structures of both deoxy and oxy forms of this r Hb. This sphere includes only one α96Trp residue for calculation purposes.

The average simulated structure of Hb A and r Hb (α96Val→Trp) in the deoxy form was prepared by the molecular graphics program, GRAPHX, developed at the Pittsburgh Supercomputing Center, Pittsburgh, Pa. The average simulated structure in the deoxy form from these side-chain angles suggests new interfacial hydrogen bonds between α96Trp and β99Asp in addition to the existing hydrogen bonds between β99Asp and α42Tyr and between β99Asp and α97Asn. Further 100-ps MD simulations of the transformed mutant Hb (α96Val→Trp) in the deoxy form suggest that these hydrogen bonds in the $\alpha_1\beta_2$ subunit interface are very stable, i.e., with average simulated distances of 2.25±0.19 angstroms and 2.32±0.22 angstroms between α42Tyr and β99Asp, and 2.22±0.34 angstroms between α97Asn and β99Asp, respectively.

Although there is no experimentally measured value for the free energy of cooperativity for r Hb (α96Val→Trp), the relatively high Hill coefficient of r Hb (α96Val→Trp) ($n_{max}$=2.6 at pH 7.4), which is quite comparable to that of Hb A, suggests that the free energy of cooperativity for r Hb (α96Val→Trp) is close to that of Hb A ($n_{max}$=3.0 at pH 7.4). The calculated value for the difference in the free energy of cooperativity between r Hb (α96Val→Trp) and Hb A is −1.5 kcal/mol per interface, as shown in Table 4 below, which is about the expected value for an Hb which has a slightly lower cooperativity than Hb A (Turner, G. J., et al., Proteins: 14 333 (1992), the disclosure of which is incorporated herein by reference).

TABLE 4

| | (kcal/mole) | | |
|---|---|---|---|
| Contribution | ΔG(deoxy) | ΔG(Oxy) | ΔΔG |
| Solvent | 0.3 | −5.0 | −5.3 |
| Protein | | | |
| α94Asp | −0.8 | −1.3 | −0.5 |
| α97Asn | −1.9 | −0.7 | 1.2 |
| β99Asp | −12.2 | 2.6 | 14.8 |
| β101Glu | 0.1 | −0.8 | −0.9 |
| β102Asn | 0.5 | −0.8 | −1.3 |
| Self (α96Val→Trp) | −24.9 | −32.0 | −7.8 |
| Total | −37.6 | −39.1 | −1.5 |

All values are given for one $\alpha_1\beta_2$ interface. Only residues that contribute more than 0.5 kcal in either the deoxy or oxy form are listed. The positive sign given in ΔG signifies a contribution destabilizing the Hb (α96Val→Trp) relative to Hb A. ΔΔG is ΔG(oxy) - ΔG(deoxy), which corresponds to the difference of free energy of cooperativity between Hb (α96Val→Trp) and Hb A.

Thus, the MD simulation results may be used advantageously to obtain information about the specific interactions which contribute to the total free energy of cooperativity. The contributions of each individual amino acid to the total free energy of cooperativity are also shown in Table 4. Most individual amino acids contribute less than 1.0 kcal, indicating that the tryptophan introduced into the $\alpha_1\beta_2$ interface does not cause large conformational changes. The largest contribution to the total free energy of cooperativity comes from the interaction with β99Asp (14.8 kcal), which most likely results from the stabilization in the deoxy-structure (−12.2 kcal). These results suggest that the new hydrogen bond between α96Trp and β99Asp may be responsible for the stabilization of the deoxy structure of this r Hb.

The r Hb (α96Val→Trp) of the present invention must be cross-linked before it can be used as a component of a blood substitute or therapeutic agent in order to prevent the dissociation of the molecule into dimers. While practically all the hemoglobin in the red cell is in the tetrameric state, circulating cell-free hemoglobin, such as in a blood substitute, would dissociate into dimers to such an extent that would lead to blockage of the glomerular membrane of the kidney, as well as the continuous drainage of the infused tetrameric hemoglobin from circulation. The hemoglobin must be cross-linked to prevent this dissociationary clearance.

Hemoglobin may be cross-linked between the a chains, such as by diisothiocyanato benzene sulfonate, within the hemoglobin tetramer, such as by pyridoxal and derivatives and acylphosphates. See, Winslow, R. M., et al., eds. *Blood Substitutes Physiological Basis of Efficacy* (Birkhauser, Boston, Mass.) pp. 82–84 (1995), the disclosure of which is incorporated herein by reference. See also, Winslow, R. M. *Hemoglobin-Based Red Cell Substitutes* (Johns Hopkins University Press, Baltimore, Md.) (1992); Manning. L. R., et al., *Biochemistry* 27:6640 (1988); Benesch, R. E., et al., *Biochem. Biophys. Res. Comm.* 156:9 (1988); Bucci, E., et al., *J. Biol. Chem.* 264:6191 (1989); Chang, T. M. S., et al., eds. Proceeding of II International Symposium on Blood Substitutes, *Biomater. Artif. Cells Artif. Organs* (1988); Kluger, R., et al., *Biochemistry* 31:7551 (1992); and DeVenuto, F., et al., *Surg. Gynecol. Obstet.* 155:342 (1982), the disclosures of which are incorporated herein by reference.

Purified cross-linked r Hb ($\alpha$96Val→Trp) that is appropriately cross-linked can then be incorporated into a hemoglobin-based blood substitute that is physiologically acceptable according to methods known in the art. See, R. M. Winslow, et al., Eds. *Blood Substitutes Physiological Basis of Efficacy* (Birkhauser, Boston, Mass.) (1995), the disclosure of which is incorporated herein by reference.

Although the invention has been described in detail for the purposes of illustration, it is to be understood that such detail is solely for that purpose and that variations can be made therein by those skilled in the art without departing from the spirit and scope of the invention except as it may be limited by the claims.

We claim:

1. A non-naturally occurring mutant human hemoglobin wherein the valine residue at position 96 of the α chain (SEQ ID NO: 1) is replaced by a tryptophan residue.

2. The hemoglobin of claim 1 possessing low oxygen affinity as compared to normal human adult hemoglobin.

3. The hemoglobin of claim 2 further possessing high cooperativity in oxygen binding.

4. The hemoglobin of claim 3 produced recombinantly.

5. r Hb (α96Val→Trp) (SEQ ID NO: 1).

6. An artificial mutant human hemoglobin which in a cell-free environment has oxygen binding properties comparable to those of human normal adult hemoglobin in red blood cells wherein said hemoglobin contains a mutation of the valine residue at position 96 of the α chain (SEQ ID NO: 1).

7. The hemoglobin of claim 23 wherein said valine residue is replaced by a tryptophan residue.

8. The hemoglobin of claim 7 which is produced recombinantly.

9. A non-naturally occurring low oxygen affinity mutant hemoglobin that has oxygen binding properties comparable to those of human normal adult hemoglobin in the presence of the allosteric effector 2,3-diphosphoglycerate, wherein the valine residue at position 96 of the α chain is replaced by a tryptophan residue (SEQ ID NO: 1).

10. A non-naturally occurring mutant hemoglobin wherein said hemoglobin contains a mutation of the valine residue at position 96 of the α chain (SEQ ID NO: 1) possessing oxygen-binding properties of oxygen affinity as measured by $P_{50}$ and cooperativity as measured by the Hill coefficient ($n_{max}$) similar to those of Hb a in the presence of the allosteric effector 2,3-diphosphoglycerate as follows: $P_{50}$ about 26.6, $n_{max}$ about 2.4 at pH 6.5; $P_{50}$ about 22.0, $n_{max}$ about 2.5 at pH 6.8; $P_{50}$ about 11.6, $n_{max}$ about 2.6 at pH 7.4; $P_{50}$ about 5.6, $n_{max}$ about 2. 4 at pH 8.0.

11. r Hb (α96Val→Trp) (SEQ ID NO: 1) derived from cells transformed with plasmid pHE202.

12. r Hb (α96Val→Trp) (SEQ ID NO: 1) derived form cells transformed with plasmid pHE702.

13. A non-toxic pharmaceutical composition comprising a non-naturally occurring mutant hemoglobin wherein the valine residue at position 96 of the α chain is replaced by a tryptophan residue (SEO ID NO: 1) in a pharmaceutically acceptable carrier.

14. The composition of claim 13 wherein said hemoglobin in a cell-free envirnoment has oxygen binding properties lower than those of human normal adult hemoglobin.

15. The composition of claim 19 wherein said hemoglobin is r Hb (α96Val→Trp) (SEQ ID NO: 1).

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 429 base pairs
        ( B ) TYPE: nucleic acid
        ( C ) STRANDEDNESS: single
        ( D ) TOPOLOGY: linear ( i i ) MOLECULE TYPE: cDNA
        ( A ) DESCRIPTION: human -globin [96ValTrp]
            cDNA coding sequence and amino acid sequence ( x i ) SEQUENCE DESCRIPTION: SEQ ID NO: 1:

```
ATG  GTG  CTG  TCT  CCT  GCC  GAC  AAG  AAC  ACC  GTC  AAG  GCC  GCC  TGG        45
Val  Leu  Ser  Pro  Ala  Asp  Lys  Thr  Asn  Val  Lys  Ala  Ala  Trp
 1                    5                        10

GGT  AAG  GTC  GGC  GCG  CAC  GCT  GGC  GAG  TAT  GGT  GCG  GAG  GCC  CTG        90
Gly  Lys  Val  Gly  Ala  His  Ala  Gly  Glu  Tyr  Gly  Ala  Glu  Ala  Leu
15                        20                       25

GAG  AGG  ATG  TTC  CTG  TCC  TTC  CCC  ACC  ACC  AAG  ACC  TAC  TTC  CCG       135
Glu  Arg  Met  Phe  Leu  Ser  Phe  Pro  Thr  Thr  Lys  Thr  Tyr  Phe  Pro
30                        35                       40

CAC  TTC  GAT  CTG  AGC  CAC  GGC  TCT  GCC  CAG  GTT  AAG  GGC  CAC  GGC       180
His  Phe  Asp  Leu  Ser  His  Gly  Ser  Ala  Gln  Val  Lys  Gly  His  Gly
45                        50                       55

AAG  AAG  GTG  GCC  GAC  GCG  CTG  ACC  AAC  GCC  GTG  GCG  CAC  GTG  GAC       225
Lys  Lys  Val  Ala  Asp  Ala  Leu  Thr  Asn  Ala  Val  Ala  His  Val  Asp
60                        65                       70

GAC  ATG  CCC  AAC  GCG  CTG  TCC  GCC  CTG  AGC  GAC  CTG  CAC  GCG  CAC       270
Asp  Met  Pro  Asn  Ala  Leu  Ser  Ala  Leu  Ser  Asp  Leu  His  Ala  His
75                        80                       85

AAG  CTT  CGG  GTG  GAC  CCA  TGG  AAC  TTC  AAG  CTC  CTA  AGC  CAC  TGC       315
Lys  Leu  Arg  Val  Asp  Pro  Trp  Asn  Phe  Lys  Leu  Leu  Ser  His  Cys
90                        95                      100

CTG  CTG  GTG  ACC  CTG  GCC  GCC  CAC  CTC  CCC  GCC  GAG  TTC  ACC  CCT       360
Leu  Leu  Val  Thr  Leu  Ala  Ala  His  Leu  Pro  Ala  Glu  Phe  Thr  Pro
105                      110                      115

GCG  GTG  CAC  GCC  TCC  CTG  GAC  AAG  TTC  CTG  GCT  TCT  GTG  AGC  ACC       405
Ala  Val  His  Ala  Ser  Leu  Asp  Lys  Phe  Leu  Ala  Ser  Val  Ser  Thr
120                      125                      130

GTG  CTG  ACC  TCC  AAA  TAC  CGT  TAA                                          429
```

```
Val  Leu  Thr  Ser  Lys  Tyr  Arg
135            140
```

( 2 ) INFORMATION FOR SEQ ID NO:2:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein
        ( A ) DESCRIPTION: human -globin [96ValTrp]
              amino acid sequence ( x i ) SEQUENCE DESCRIPTION: SEQ ID NO: 2:

```
Val  Leu  Ser  Pro  Ala  Asp  Lys  Thr  Asn  Val  Lys  Ala  Ala  Trp
1                   5                        10

Gly  Lys  Val  Gly  Ala  His  Ala  Gly  Glu  Tyr  Gly  Ala  Glu  Ala  Leu
15                       20                       25

Glu  Arg  Met  Phe  Leu  Ser  Phe  Pro  Thr  Thr  Lys  Thr  Tyr  Phe  Pro
30                       35                       40

His  Phe  Asp  Leu  Ser  His  Gly  Ser  Ala  Gln  Val  Lys  Gly  His  Gly
45                       50                       55

Lys  Lys  Val  Ala  Asp  Ala  Leu  Thr  Asn  Ala  Val  Ala  His  Val  Asp
60                       65                       70

Asp  Met  Pro  Asn  Ala  Leu  Ser  Ala  Leu  Ser  Asp  Leu  His  Ala  His
75                       80                       85

Lys  Leu  Arg  Val  Asp  Pro  Trp  Asn  Phe  Lys  Leu  Leu  Ser  His  Cys
90                       95                       100

Leu  Leu  Val  Thr  Leu  Ala  Ala  His  Leu  Pro  Ala  Glu  Phe  Thr  Pro
105                      110                      115

Ala  Val  His  Ala  Ser  Leu  Asp  Lys  Phe  Leu  Ala  Ser  Val  Ser  Thr
120                      125                      130

Val  Leu  Thr  Ser  Lys  Tyr  Arg
135            140
```

( 2 ) INFORMATION FOR SEQ ID NO:3:

( i ) SEQUENCE CHARACTERISTICS:
        ( A ) LENGTH: 444 base pairs
        ( B ) TYPE: nucleic acid
        ( C ) STRANDEDNESS: single
        ( D ) TOPOLOGY: linear ( i i ) MOLECULE TYPE: cDNA
        ( A ) DESCRIPTION: human -globin cDNA coding
              sequence and amino acid sequence ( x i ) SEQUENCE DESCRIPTION: SEQ ID NO: 3:

```
ATG  GTG  CAC  CTG  ACT  CCT  GAG  GAG  AAG  TCT  GCC  TGG  ACT  GCC  CTG      45
Val  His  Leu  Thr  Pro  Glu  Glu  Lys  Ser  Ala  Trp  Thr  Ala  Leu
1                   5                        10

TGG  GGC  AAG  GTG  AAC  GTG  GAT  GAA  GTT  GGT  GGT  GAG  GCC  CTG  GGC      90
Trp  Gly  Lys  Val  Asn  Val  Asp  Glu  Val  Gly  Gly  Glu  Ala  Leu  Gly
15                       20                       25

AGG  CTG  CTG  GTG  GTC  TAC  CCT  TGG  ACC  CAG  AGG  TTC  TTT  GAG  TCC     135
Arg  Leu  Leu  Val  Val  Tyr  Pro  Trp  Thr  Gln  Arg  Phe  Phe  Glu  Ser
30                       35                       40

TTT  GGG  GAT  CTG  TCC  ACT  CCT  GAT  GCT  GTT  ATG  GGC  AAC  CCT  AAG     180
Phe  Gly  Asp  Leu  Ser  Thr  Pro  Asp  Ala  Val  Met  Gly  Asn  Pro  Lys
45                       50                       55

GTG  AAG  GCT  CAT  GGC  AAG  AAA  GTG  CTC  GGT  GCC  TTT  AGT  GAT  GGC     225
Val  Lys  Ala  His  Gly  Lys  Lys  Val  Leu  Gly  Ala  Phe  Ser  Asp  Gly
```

```
CTG  GCT  CAC  CTG  GAC  AAC  CTC  AAG  GGC  ACC  TTT  GCC  ACA  CTG  AGT        270
Leu  Ala  His  Leu  Asp  Asn  Leu  Lys  Gly  Thr  Phe  Ala  Thr  Leu  Ser
75                       80                       85

GAG  CTG  CAC  TGT  GAC  AAG  CTG  CAC  GTG  GAT  CCT  GAG  AAC  TTC  AGG        315
Glu  Leu  His  Cys  Asp  Lys  Leu  His  Val  Asp  Pro  Glu  Asn  Phe  Arg
90                       95                       100

CTC  CTG  GGC  AAC  GTG  CTG  GTC  TGT  GTG  CTG  GCC  CAT  CAC  TTT  GGC        360
Leu  Leu  Gly  Asn  Val  Leu  Val  Cys  Val  Leu  Ala  His  His  Phe  Gly
105                      110                      115

AAA  GAA  TTC  ACC  CCA  CCA  GTG  CAG  GCT  GCC  TAT  CAG  AAA  GTG  GTG        405
Lys  Glu  Phe  Thr  Pro  Pro  Val  Gln  Ala  Ala  Tyr  Gln  Lys  Val  Val
120                      125                      130

GCT  GGT  GTG  GCT  AAT  GCC  CTG  GCC  CAC  AAG  TAT  CAC  TAA                  444
Ala  Gly  Val  Ala  Asn  Ala  Leu  Ala  His  Lys  Tyr  His
135                      140                      145
```

( 2 ) INFORMATION FOR SEQ ID NO:4:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein
        ( A ) DESCRIPTION: human -globin amino acid
            sequence ( x i ) SEQUENCE DESCRIPTION: SEQ ID NO: 4:

```
Val  His  Leu  Thr  Pro  Glu  Glu  Lys  Ser  Ala  Trp  Thr  Ala  Leu
1                        5                        10

Trp  Gly  Lys  Val  Asn  Val  Asp  Glu  Val  Gly  Gly  Glu  Ala  Leu  Gly
15                       20                       25

Arg  Leu  Leu  Val  Val  Tyr  Pro  Trp  Thr  Gln  Arg  Phe  Phe  Glu  Ser
30                       35                       40

Phe  Gly  Asp  Leu  Ser  Thr  Pro  Asp  Ala  Val  Met  Gly  Asn  Pro  Lys
45                       50                       55

Val  Lys  Ala  His  Gly  Lys  Lys  Val  Leu  Gly  Ala  Phe  Ser  Asp  Gly
60                       65                       70

Leu  Ala  His  Leu  Asp  Asn  Leu  Lys  Gly  Thr  Phe  Ala  Thr  Leu  Ser
75                       80                       85

Glu  Leu  His  Cys  Asp  Lys  Leu  His  Val  Asp  Pro  Glu  Asn  Phe  Arg
90                       95                       100

Leu  Leu  Gly  Asn  Val  Leu  Val  Cys  Val  Leu  Ala  His  His  Phe  Gly
105                      110                      115

Lys  Glu  Phe  Thr  Pro  Pro  Val  Gln  Ala  Ala  Tyr  Gln  Lys  Val  Val
120                      125                      130

Ala  Gly  Val  Ala  Asn  Ala  Leu  Ala  His  Lys  Tyr  His
135                      140                      145
```

( 2 ) INFORMATION FOR SEQ ID NO:5:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Hyun-Won Kim
            Tong-Jian Shen Dazhen Philip Sun
Nancy T. Ho
Marcella Madrid
Chien Ho
(B) TITLE: A Novel Low Oxygen
Affinity Recombinant Hemoglobin
(96 Val Trp): Switching Quaternary
Structure Without Changing the Ligtion
State
(C) JOURNAL: Journal of Molecular Biology
(D) VOLUME: 248
(E) ISSUE: 4
(F) PAGES: 867-882
(G) DATE: 00-MAY-95
(K) RELEVANT RESIDUES IN SEQ ID NO: 1: 1 to 21

(x i) SEQUENCE DESCRIPTION: SEQ ID NO: 5:

TTTGAAGTTC CATGGATCAA C 21

(2) INFORMATION FOR SEQ ID NO:6:

(i) SEQUENCE CHARACTERISTICS:
(A) LENGTH: 25 nucleotides
(B) TYPE: nucleic acid
(C) STRANDEDNESS: single
(D) TOPOLOGY: linear (i i) MOLECULE TYPE: synthetic DNA (x i) SEQUENCE DESCRIPTION: SEQ ID NO: 6:

AGCTTGAAGT TCCATGGGTC CACCC 25

(2) INFORMATION FOR SEQ ID NO:7:

(i) SEQUENCE CHARACTERISTICS:
(A) LENGTH: 29 nucleotides
(B) TYPE: nucleic acid
(C) STRANDEDNESS: single
(D) TOPOLOGY: linear (i i) MOLECULE TYPE: synthetic DNA (x i) SEQUENCE DESCRIPTION: SEQ ID NO: 7:

GAGAACCCCA TATGGTGCTG TCTCCTGCC 29

(2) INFORMATION FOR SEQ ID NO:8:

(i) SEQUENCE CHARACTERISTICS:
(A) LENGTH: 32 nucleotides
(B) TYPE: nucleic acid
(C) STRANDEDNESS: single
(D) TOPOLOGY: linear (i i) MOLECULE TYPE: synthetic DNA (x i) SEQUENCE DESCRIPTION: SEQ ID NO: 8:

CCGAGGCACT AGTTTAACGG TATTTGGAGG TC 32

(2) INFORMATION FOR SEQ ID NO:9:

(i) SEQUENCE CHARACTERISTICS:
(A) LENGTH: 36 nucleotides
(B) TYPE: nucleic acid
(C) STRANDEDNESS: single
(D) TOPOLOGY: linear (i i) MOLECULE TYPE: synthetic DNA (x i) SEQUENCE DESCRIPTION: SEQ ID NO: 9:

CAAACAGACC ATATGGTGCA CCTGACTCCT GAGGAG 36

( 2 ) INFORMATION FOR SEQ ID NO:10:

( i ) SEQUENCE CHARACTERISTICS:
        ( A ) LENGTH: 37 nucleotides
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO: 10:

AGCAAGAATG  CATGCTTAGT  GATACTTGTG  GGCCAGG        37

( 2 ) INFORMATION FOR SEQ ID NO:11:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO: 11:

TGGACAGAAT  TCCATGGCTA  TCTCAATCA        29

( 2 ) INFORMATION FOR SEQ ID NO:12:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO: 12:

TGGCTTAAGC  TTATTCGTCG  TGCGAG        26